United States Patent
Alsalem

(10) Patent No.: US 9,364,713 B2
(45) Date of Patent: Jun. 14, 2016

(54) DEVICE AND METHOD TO CONFIGURE GYM EXERCISES

(71) Applicant: Abdullah Khaled Alsalem, Riyadh (SA)

(72) Inventor: Abdullah Khaled Alsalem, Riyadh (SA)

( * ) Notice: Subject to any disclaimer, the term of this patent is extended or adjusted under 35 U.S.C. 154(b) by 235 days.

(21) Appl. No.: 14/150,279

(22) Filed: Jan. 8, 2014

(65) Prior Publication Data

US 2015/0190677 A1    Jul. 9, 2015

(51) Int. Cl.
| | | |
|---|---|---|
| *G06F 19/00* | (2011.01) | |
| *A63B 24/00* | (2006.01) | |
| *A63B 71/06* | (2006.01) | |
| *A63B 22/00* | (2006.01) | |
| *A63B 22/02* | (2006.01) | |
| *A63B 22/06* | (2006.01) | |

(52) U.S. Cl.
CPC ......... *A63B 24/0075* (2013.01); *A63B 22/0048* (2013.01); *A63B 22/02* (2013.01); *A63B 22/0605* (2013.01); *A63B 24/0062* (2013.01); *A63B 71/06* (2013.01); *A63B 2024/0065* (2013.01); *A63B 2024/0093* (2013.01); *A63B 2220/806* (2013.01); *A63B 2225/50* (2013.01); *A63B 2230/015* (2013.01)

(58) Field of Classification Search
USPC ..................................... 700/91–93; 482/8, 9
See application file for complete search history.

(56) References Cited

U.S. PATENT DOCUMENTS

| | | | |
|---|---|---|---|
| 7,063,644 B2 | 6/2006 | Albert et al. | |
| 7,172,530 B1 | 2/2007 | Hercules | |
| 7,601,099 B2 | 10/2009 | Kang | |
| 7,717,827 B2 | 5/2010 | Kurunmäki et al. | |
| 7,914,419 B2 | 3/2011 | Karkanias et al. | |
| 8,128,532 B2* | 3/2012 | Chen ...................... | G06Q 10/02 482/1 |
| 8,150,707 B2 | 4/2012 | Hayet et al. | |
| 8,235,871 B2 | 8/2012 | Mikan et al. | |
| 2006/0166737 A1* | 7/2006 | Bentley ................ | A61B 5/1122 463/30 |
| 2006/0201580 A1* | 9/2006 | Kang ..................... | A63B 69/00 144/195.5 |
| 2010/0009810 A1 | 1/2010 | Trzecieski | |
| 2012/0179278 A1 | 7/2012 | Riley et al. | |
| 2012/0183940 A1* | 7/2012 | Aragones ............ | G06F 19/3437 434/247 |

OTHER PUBLICATIONS

Chris Williams and Rahul Peravali, "TreadSmart, a RFID Treadmill", Dec. 9, 2008, ECE 445 Senior Design, p. 1-31.

* cited by examiner

*Primary Examiner* — Ronald Laneau
(74) *Attorney, Agent, or Firm* — Oblon, McClelland, Maier & Neustadt, L.L.P

(57) ABSTRACT

Described herein is a gym exercise controller device that configures workout routines. The controller allows the user to create a daily workout regimen and also incorporates a workout skip calculation. The controller tracks the performance of a user on the respective exercises apparatuses and provides the user an option to change his/her workout routine based on a performance parameter of the user as well as a comparison of the user's performance parameter to the performance parameter of a group of users.

20 Claims, 14 Drawing Sheets

DEVICE AND METHOD TO CONFIGURE GYM EXERCISES

GRANT OF NON-EXCLUSIVE RIGHT

This application was prepared with financial support from the Saudia Arabian Cultural Mission, and in consideration therefore the present inventor(s) has granted The Kingdom of Saudi Arabia a non-exclusive right to practice the present invention.

FIELD OF THE DISCLOSURE

The present disclosure relates to a gymnasium exercise system for assisting a user in training with exercise devices in a fitness gymnasium. The system provides the user an option to dynamically change his/her workout routine based on the user's skill level and a performance parameter and further incorporates a social aspect by which a user can decide his/her workout routine. Further, the user may select a workout routine (exercises) based on his/her medical or body condition.

BACKGROUND

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Training in a fitness gymnasium usually includes exercise devices such as treadmills, bicycles, steppers, bench-weights and the like. Frequently, users may not know how to properly use such training devices and thereby result in either overusing the devices in an improper manner that may lead to bodily injuries or under-using the devices which results in the user not achieiveing his/her expected amount of weight loss. Such experiences may prove to be disappointing for the user who may eventually lose interest in the fitness gymnasium.

Recently, experienced personnel such as a personal trainer or the like have become increasing popular in a gymnasium setting. The personal trainer may be able to guide the user workout by way of selecting suitable exercises, which exercise device to use, setting up the selected exercise device, selecting suitable workout durations, tracking performance by way of updating and reviewing workout records and the like. However, hiring such a personal trainer is usually cost prohibitive and moreover includes a workout regiment that is decided in advance by the trainer.

Moreover, while using the personal trainer, the exercise routine includes a fixed set of exercises that are performed by the user over a certain time duration. The exercise routine is fixed for each user and does not include the provision to compare the users performance to the performance of a group of users. Furthermore, in such a setting, the user does not have the provision to configure his/her exercise routine based on the exercise routines performed by a group of users.

SUMMARY

Aspects of the present disclosure provide a controller device comprising: circuitry configured to list a plurality of exercises that are available to be performed by a user based on a skill level of the user; receive a selection of the plurality of exercises from the user and determine whether the selected exercises are permitted to be performed by the user; compute a performance index for the user based on a target weight loss and an actual weight loss achieved by the user; compute an overall performance of the user based on the performance index, a first parameter and a second parameter; determine whether the exercises performed by the user are permitted skipped for a predetermined time based on the performance index of the user; determine, based on the overall performance of the user whether there is a transition in the user's skill level; and determine the user's exercises for future performance based on exercises performed by members of a group.

According to another embodiment is a provided a method. The method includes listing a plurality of exercises that are available to be performed by a user based on a skill level of the user; receiving a selection of the plurality of exercises from the user and determining whether the selected exercises are permitted to be performed by the user; computing a performance index for the user based on a target weight loss and an actual weight loss achieved by the user; computing an overall performance of the user based on the performance index, a first parameter and a second parameter; determining whether the exercises performed by the user are permitted skipped for a predetermined time based on the performance index of the user; determining, based on the overall performance of the user whether there is a transition in the user's skill level; and determining the user's exercises for future performance based on exercises performed by members of a group.

According to another embodiment is provided a non-transitory computer readable medium having stored thereon a program that when executed by a computer causes the computer to execute a method, the method includes: listing a plurality of exercises that are available to be performed by a user based on a skill level of the user; receiving a selection of the plurality of exercises from the user and determining whether the selected exercises are permitted to be performed by the user; computing a performance index for the user based on a target weight loss and an actual weight loss achieved by the user; computing an overall performance of the user based on the performance index, a first parameter and a second parameter; determining whether the exercises performed by the user are permitted to be skipped for a predetermined time based on the performance index of the user; determining, based on the overall performance of the user whether there is a transition in the user's skill level; and determining the user's exercises for future performance based on exercises performed by members of a group.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
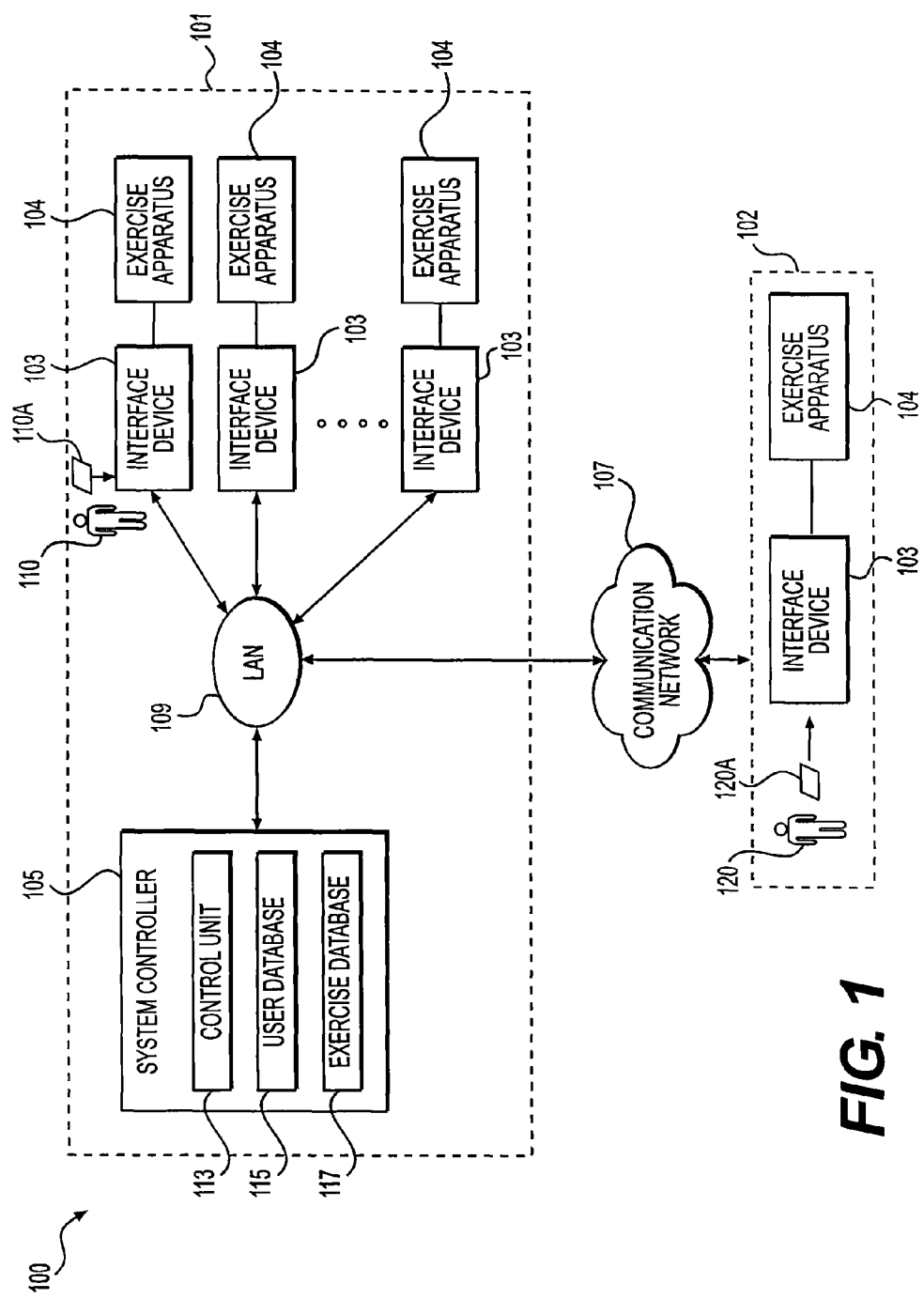
FIG. 1 is a schematic diagram of a gymnasium exercise support system according to one embodiment.

Referring now to the drawings, wherein like reference numerals designate identical or corresponding parts throughout the several views.

FIG. 1 is a schematic diagram of a gymnasium (gym) exercise system 100 according to one embodiment of the disclosure. The gym exercise system of the present embodiment includes a plurality of interface devices 103 and a system controller 105. The gym system 100 may be operated with a plurality of exercise devices 104 arranged in fitness gyms 101 and 102. The exercise devices 104 may be any type of exercise device such as a treadmill, a bicycle, a stepper, a bench-weight or the like. The plurality of interface devices 103 and the system controller 105 are coupled to each other with a local area network (LAN) 109. The fitness gym 102 may have a dedicated system controller assigned to it or may access a centralized system controller (for example, 105). The gym 102 may be connected to the gym 101 by a communication network 107. The LAN 109 and the communication network 107 may be a wireless communication network or a wired communication network.

To gain access to the gym exercise system 100, a user 110 (or user 120) may perform a 'login' operation at any one of the interface device 103 using a device 110A (or 120A). The device 110A stores identification information of the user 110. According to an embodiment, the device 110A may include a nonvolatile memory storing the identification information that is assigned to each user. Each user uses his/her own user device 110A to access the gym exercise support system. The user device 110A may be an electronic card including an IC tag or a RFID tag. Alternatively, the device 110A may be a mobile phone on which coded identification information is stored. The device 110A may communicate with the interface device 103 using near field communication technology or the like. The interface devices 103 may also be configured to magnetically or optically read coded identification information on the user device 110A. According to another embodiment, the user may perform the login operation without using any input device 110A. For example, the interface device 103 may be configured to include an image detector that is configured to detect a user's face, or the interface device 103 may include any other biometric identifier that can identify for example, the user finger print in order to perform the login operation. In such instances, the system 100 can be operated without the input device 110A.

The gym exercise support system allows the user 110 or 120, to create a daily workout regimen for a particular day (to be discussed later). The daily workout regimen includes a list of exercises that may be performed by the user 110 and a target workout amount of the respective exercises. The gym exercise support system monitors the workout of the user 110 (or 120) and keeps a track record of his/her performance (to be discussed later).

In the present embodiment, of the plurality of interface devices 103, one interface device is placed in the fitness gym 102, and the remaining interface devices 103 are placed in the fitness gym 101. The interface device 103 in gym 102 is coupled to the system controller 105 and the other interface devices 103 in the fitness gym 101, via the LAN 109 and the communication network 107 such as Internet, wide area network (WAN) or another local area network (LAN) or any combination thereof. Alternatively, all the interface devices 200 may be arranged in a single fitness gym or more than two different fitness gyms.

The system controller 105 includes a control unit 113, a user database 115, and an exercise database 117. The control unit 113 controls the overall operation of the gym exercise system and executes processes that assist the user in determining workout exercises. The user database 115 and the exercise database 117 store data to be used during the operation of the gym exercise system.

The user database 115 stores user profile information for all users. For each user, the user profile information may include, but is not limited to, identification information, personal information such as weight, height, age, the daily workout regimen, expected weight loss, and the like. The user profile information may further include data for each user corresponding to a particular exercise such as a user skill level, an exercise group to which the user belongs, a weekly target workout amount, a total workout amount in the current week, workout history, planned and actual gym visit days in the current week, and a performance index.

The user skill level and the exercise group may be selected by the user during registration. The total amount of workout to be performed by a user in a week includes all the exercises performed in the fitness gyms and all the physical activities performed outside the fitness gyms. The weekly target workout amount is a target set by the user regarding the total amount of workout in a single week. The workout history is a list of all the exercises performed in the gyms and the physical activities performed outside the fitness gyms in the current week, and actual performances of the respective exercises and the physical activities. The performance index is parameter that tracks the progress of user and may be, for example, a weight loss since the start of gym exercises, a weekly weight loss, a ratio of the weekly weight loss to the total workout amount per week, or the like. Specific details regarding the user skill level, performance determination and the like are described in detail later with reference to FIGS. 6-12.

The exercise database 117 stores exercise information for respective exercises to be performed with the exercise devices 104. For each exercise, the exercise information may include, but is not limited to, information on the exercise machine to be used, machine setup parameters to configure the equipment based on the user's preference, in order to allow the user to perform the exercise, suitable skill levels for performing the exercise, upper limits on the time duration for the respective skill levels of the users, and upper limits on workout amount (possibly in time) per day (or week) of the exercise for the respective skill levels The system controller 105 of the present embodiment maintains and processes all pertinent information related to the user and his/her workout routine. Alternatively, according to another embodiment, the user device 110A can also be configured to store the user's profile information and further determine the user's workout routine. Accordingly, every time the interface device 103 reads the identification information from the user device 110A, the system controller 105 may be updated with the latest user information and this information may be stored in the system controller for back up purposes. Additionally, the most current version of the user profile information may also be transferred to the user device 110A from the system controller 105, in cases where there is a malfunctioning of the user device 110A and it is later rebooted or reformatted and requires updated user exercise information.

Figure 2:
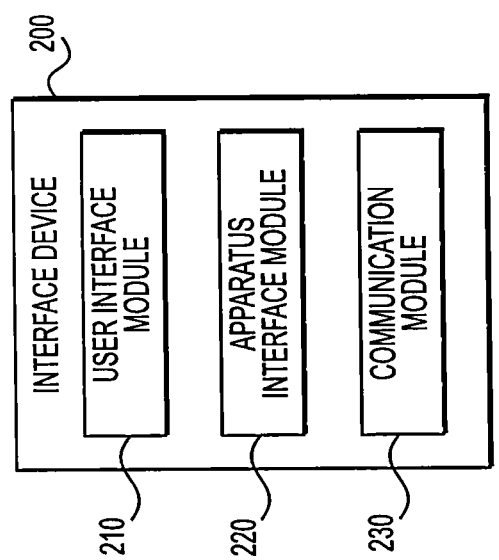
FIG. 2 depicts a schematic diagram of an interface device according to one embodiment.

FIG. 2 is a schematic diagram of an interface device 200 according to one embodiment. The interface device 200 includes a user interface module 210, an apparatus interface module 220, and a communication module 230.

The user interface module 210 interfaces between the user 110 and the gym exercise system 100. The user interface module 210 is configured to read identification information stored in the user device 110A, receive input from the user, and transmit the received input and the identification information to the system controller 105 via the communication module 230. The user interface module 210 is further configured to receive information generated by the system controller 105 in response to the received input from the user via the communication module 230, and present the received information to the user 110.

The apparatus interface module 220 interfaces between the exercise apparatus 104 and the gym exercise system. The apparatus interface module 220 receives apparatus setup parameters from the system controller 105 via the communication module 230, and transmits the received apparatus setup parameters to the exercise apparatus 104 coupled thereto.

The apparatus setup parameters configure the exercise apparatus 104 so that the user 110 may perform the exercise prescribed in the daily workout regimen with this exercise apparatus 104. The apparatus setup parameters may include, but are not limited to, an exercise program to be used, a resistance or intensity during exercise, duration or a number of repetitions of exercise. Herein, the exercise program means a preset program that controls the temporal pattern of exercise apparatus operation. For example, an exercise program "hill climbing" for a treadmill may be employed to control the operation of treadmill in such a way such that the resistance that the user feels during running is small at the commencement of the exercise and gradually increases thereafter. The exercise apparatus 104 may be configured in different ways with a different set of apparatus setup parameters so that the user 110 may be able to perform different exercises with the same exercise apparatus.

The apparatus interface module 220 monitors the workout of user 110 performing the exercise activity using the exercise apparatus 104 and transmits information indicating the performance of the user 110 to the system controller 105 via the communication module 230. The apparatus interface module 220 monitors the user workout, for example, by receiving one or more signals from the exercise apparatus 104 indicating its mechanical movements associated with the user workout movement.

Alternatively, when the exercise apparatus 104 has a workout monitoring function and outputs information indicating the user workout such as the time-duration of the workout exercise, the number of repetitions, the burnt calories, or the like. The apparatus interface module 220 may receive such information and forward the information to the system controller 105. The monitoring of the user workout may also be achieved by utilizing a camera and an image processing module in the interface device 200. The exercise performed by the user with the exercise apparatus 104, is conducted within a predetermined area surrounding the exercise apparatus 104. Specifically, the moving parts of the exercise apparatus 104 and moving body parts of the user 110 such as legs or hands move within a predetermined area during the workout. The camera in the interface device 200 may be arranged so as to capture images of these repetition movements within the predetermined area during the workout, and the image processing module may processes the captured images to detect the movements in the area, thereby making it possible to monitor the user workout without utilizing any signal or information from the exercise apparatus 104.

The apparatus interface module 220 may receive a change in any of the apparatus setup parameters from the exercise apparatus 104, when the user 110 directly changes the apparatus setup parameters. The apparatus interface module 220 transmits such changes in the apparatus setup parameters to the system controller 105 in order to update the corresponding parameter setting of the particular apparatus for the user. The updated parameter setting may be stored in the exercise database 117 and later retrieved by the user.

The communication module 230 couples the interface device 200 to the LAN 109 or the communication network 107 so as to allow the interface device 200 to communicate with the system controller 105 and any other interface device 103. The communication module 230 includes a wireless transceiver and is configured to support communications in accordance with preset wireless communication protocols.

Figure 3:
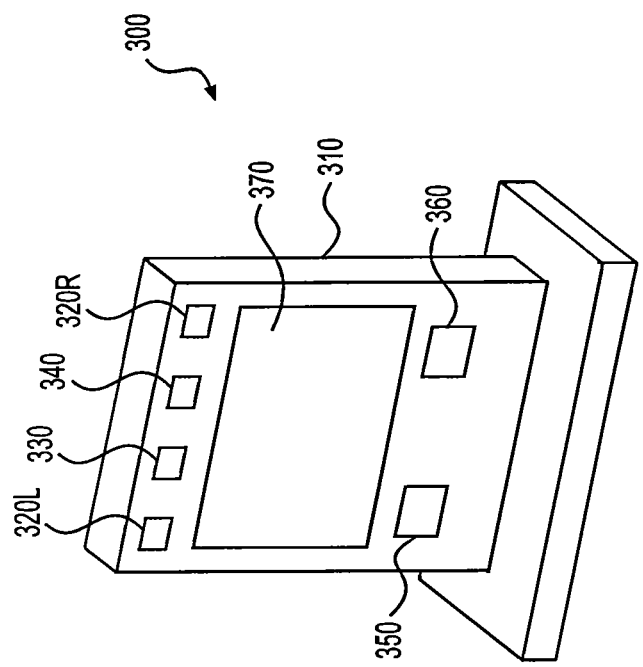
FIG. 3 is a perspective view of an interface device.

FIG. 3 is a perspective view 300 of the interface device 200 according to an embodiment of the present disclosure. The interface device 300 has a kiosk-like profile and includes a housing body 310, a reader 350 for electromagnetically or optically reading the identification information from the user device 110A, a touch-sensitive display unit 370 for receiving input from the user and presenting information to the user, and a printer 360 for printing out information. The interface device 300 further includes a camera 330, a microphone 340, and speakers 320L and 320R for audio-visual interface with the user.

The reader 350, the touch-sensitive display unit 370, the printer 360, the camera 330, the microphone 340, and the speakers 320L and 320R are hardware components included in the user interface module 210 and facilitate the interface between the user and the gym exercise system. The interface device 300 may further include a keypad and/or a pointing device to receive input from the user. The interface device 300 allows the user to easily access the gym exercise system at any time during the workout with the exercise apparatus 104 coupled thereto.

According to another embodiment, the reader 350 may be a device for identifying the user by biometric authentication. For example, the reader 350 may be a scanner for scanning a finger print of a user. In that case, the system controller 105 in FIG. 1, may store finger print data in advance for each user, and search the user by identifying the finger print data that matches the scanned finger print. Further, the touch-sensitive display unit 370 may be divided into a plurality of components. For example, the user interface module 210 may include one smaller touch-sensitive display unit that receives input from users and communicates with the system controller 105, and another display unit without the touch-sensitive capability that is used for visual communications.

Figure 4:
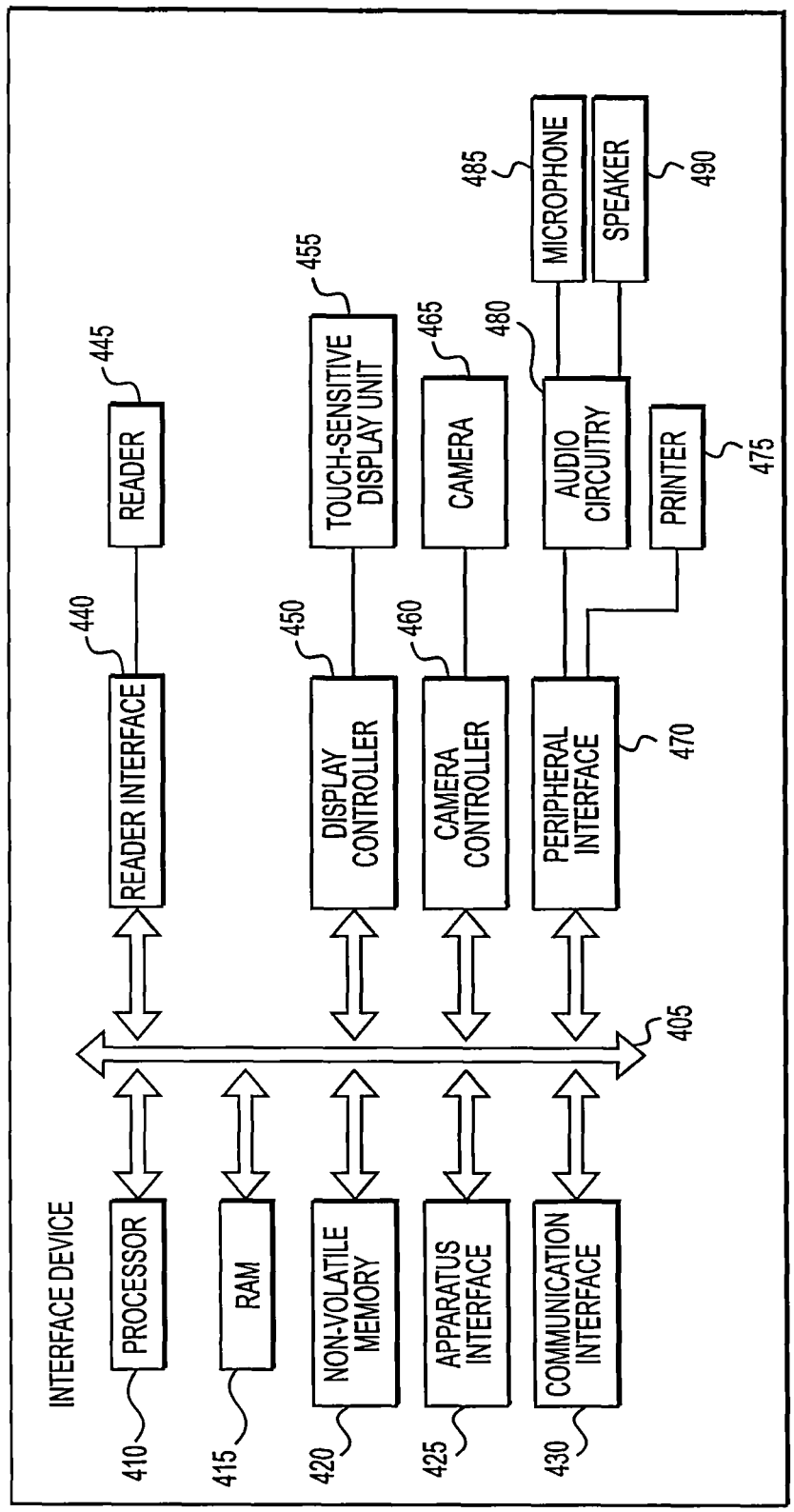
FIG. 4 is a schematic diagram of a hardware configuration of an interface device.

FIG. 4 is a schematic diagram of a hardware configuration of the interface device 200 according to one embodiment of the disclosure. The interface device includes a processor 410 that controls the entire operation of the interface device 200. The processor 410 is coupled to a random access memory (RAM) 415 and a plurality of peripheral devices via a bus 405. The processor 410 may be a central processing unit (CPU) or the like.

The RAM 415 is a primary memory device of the interface device 200. The RAM 415 temporarily stores at least part of the application programs, firmware, or programs of an operating system (OS) to be executed by the processor 410. The RAM 415 also stores data to be used in the processes executed by the processor 410.

The peripheral devices coupled to the bus 405 include a nonvolatile memory 420, a reader interface 440, a display controller 450, a camera controller 460, a peripheral interface 470, an apparatus interface 425, and a communication interface 430.

The nonvolatile memory 420 may be, for example, a hard disk drive or a semiconductor storage device such as an electrically erasable programmable read-only memory (EEPROM), a flash memory or the like. The nonvolatile memory 420 can be used as an auxiliary storage device. The reader interface 440 is coupled to the reader 445, and receives and/or sends electrical signals from/to the reader 445. The display controller 450 is coupled to the touch-sensitive display unit 445, and receives and/or sends electrical signals from/to the touch-sensitive display unit 455. The camera controller 460 is coupled to the camera 465 and receives and/or sends electrical signals from/to the camera 465.

The peripheral interface 470 is coupled to an audio circuitry 480 and the printer 475, and receives and/or sends electrical signals from/to the audio circuitry 480 and the printer 475. The audio circuitry 480 is coupled to the microphone 485 and the speaker 490. The audio circuitry 480 receives audio data from the peripheral interface 470, converts the audio data to an electrical signal, and transmits the electrical signal to the speaker 490. The audio circuitry 480 also receives electrical signals from the microphone 485, converts the electrical signals to audio data, and transmits the audio data to the peripheral interface 470 for processing.

The apparatus interface 425 couples the interface device 200 and the exercise apparatus 104, and performs input and output operations therebetween. The apparatus interface 425 receives signals and data from the exercise apparatus 104, and sends received signals and data to the processor 410 or the RAM 415. The apparatus interface 425 also receives signals and data from the processor 410 or other components, and sends received signals and data to the exercise apparatus 104.

The communication interface 430 couples the interface device 200 and the system controller 105 via the LAN 109 and/or the communication network 107, and performs input and output operations therebetween. The communication interface 430 receives signals and data from the processor 410 or the other component in the interface device 200 and transmits received signals and data to the system controller 105. The communication interface 430 also receives signals and data from the system controller 105 or another interface device 200, and transmits received signals and data to the processor 410 or the other component in the interface device 200, by using the bus 405.

Figure 5:
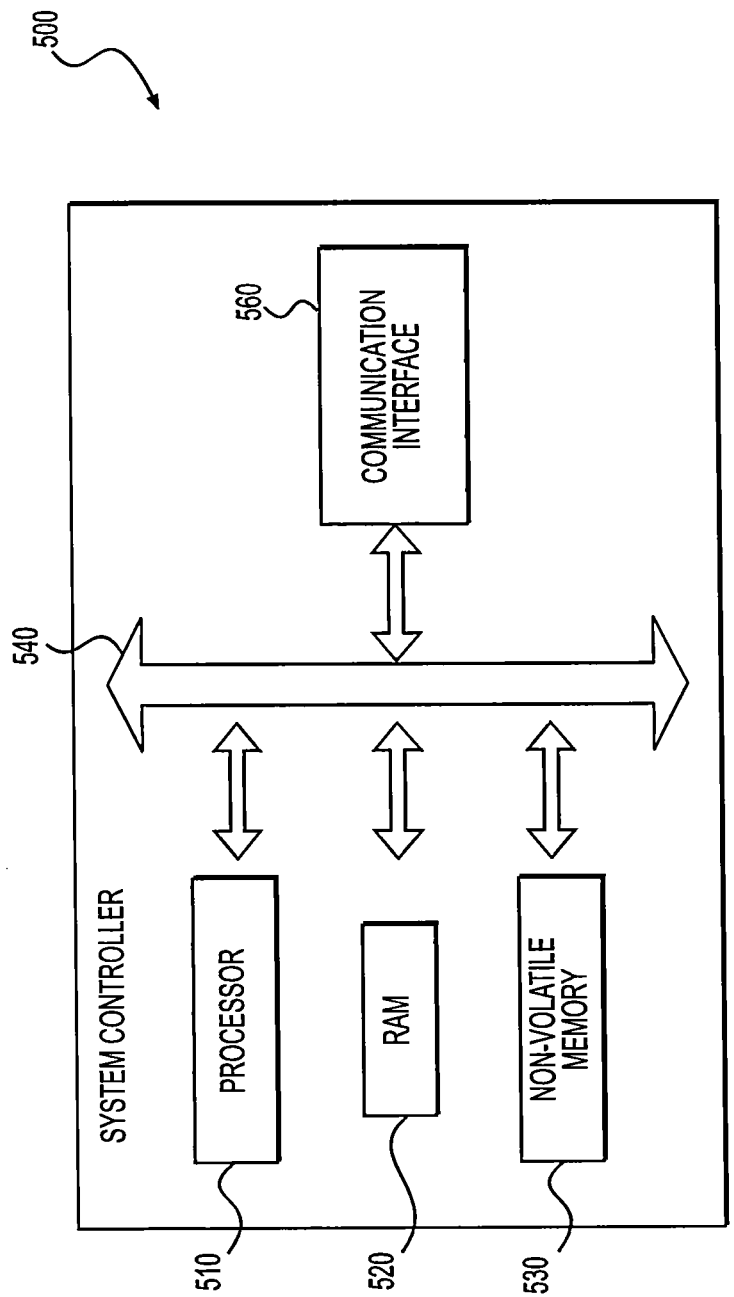
FIG. 5 is a schematic diagram of a hardware configuration of a system controller.

FIG. 5 is a schematic diagram of a hardware configuration of the system controller 105 in FIG. 1, according to an embodiment of the present disclosure. The system controller 105 includes a processor 510 that controls the entire operation of the system controller 105. The processor 510 is coupled to a random access memory (RAM) 520 and a plurality of peripheral devices via a bus 540. The processor 510 may be a central processing unit (CPU) or the like.

The RAM 520 is used as a primary memory device of the system controller 105. The RAM 520 temporarily stores at least part of application programs, firmware, or programs of an operating system (OS) to be executed by the processor 510. The RAM 520 also stores various data to be used in the processes executed by the processor 510.

The peripheral devices coupled to the bus 540 include a nonvolatile memory 530 and a communication interface 560. The communication interface 560 couples the system controller 105 and the plurality of interface devices 200, and performs input and output operations therebetween. The communication interface 560 receives signals and data from other devices and transmits the received signals and data to the processor 510 or the RAM 520.

The nonvolatile memory 530 may be, for example, a hard disk drive or a semiconductor storage device such as an electrically erasable programmable read-only memory (EEPROM), a flash memory or the like. The nonvolatile memory 530 is used as an auxiliary storage device of the system controller 105. The nonvolatile memory 530 stores an OS program, firmware, application programs, and various data. The nonvolatile memory 530 can also store data of the user database 115 and the exercise database 117.

The users in the gym system can be indexed by a variable i, wherein i takes on values in the range 1 to U. The parameter U represents the total number of users in the system. Similarly, the exercises offered by the gym system can be indexed by a variable e, wherein e takes on values in the range from 1 to E. The parameter E represents the total number of exercises offered by the system. The users of the gym may be assigned different skill levels depending on various factors such as the length of time they have been exercising, their target weight loss or the like.

According to one embodiment, the gym system uses the variable j to assign different skill levels to the users. For example, a value of j=1 may correspond to a beginner/novice (low skill level), a value of j=2 may correspond to a user with intermediate skill level (medium skill) and a value of j=3 may correspond to a user having an expert skill level (high skill level). For users of different skill levels, the system may have a predetermined expected weight loss corresponding to each exercise performed the user. This information may be represented in the form of matrix as shown below:

TABLE I

Expected weight loss for each exercise

| | | e = 1 | e = 2 | e = 3 | e = 4 | e = 5 | ... | e = E |
|---|---|---|---|---|---|---|---|---|
| W[j][e] = | j = 1 | $w_{11}$ | $w_{12}$ | $w_{13}$ | $w_{14}$ | $w_{15}$ | ... | $w_{1E}$ |
| | j = 2 | $w_{21}$ | $w_{22}$ | $w_{23}$ | $w_{24}$ | $w_{25}$ | ... | $w_{2E}$ |
| | j = 3 | $w_{31}$ | $w_{32}$ | $w_{33}$ | $w_{34}$ | $w_{35}$ | ... | $w_{3E}$ |

The matrix W[j][e] in the above embodiment is of order 3×E, for a total of three skill levels and a total of E exercises. The values $w_{ie}$ (for values of i=1, 2, 3; and e=1, 2, 3 ... E) in the matrix may be decided by the gym system in advance. Further, the system may impose a restriction on a particular exercise to be performed by users of only a certain skill level. Thus, the system may assign a value of zero to the corresponding expected weight loss for the appropriate skill level. In other words, a value of zero for the expected weight loss for a particular exercise may imply that the particular exercise is not to be performed by the user of a particular skill level.

Further, for each of the exercises offered, the system may set a predetermined number of hours that a user of particular skill has to work in order to achieve the expected weight loss. This information can also be represented in a matrix form as shown below:

TABLE II

Expected hours for each exercise based on skill level.

|  |  | e = 1 | e = 2 | e = 3 | e = 4 | e = 5 | ... | e = E |
|---|---|---|---|---|---|---|---|---|
| H[j][e] = | j = 1 | $h_{11}$ | $h_{12}$ | $h_{13}$ | $h_{14}$ | $h_{15}$ | ... | $h_{1E}$ |
|  | j = 2 | $h_{21}$ | $h_{22}$ | $h_{23}$ | $h_{24}$ | $h_{25}$ | ... | $h_{2E}$ |
|  | j = 3 | $h_{31}$ | $h_{32}$ | $h_{33}$ | $h_{34}$ | $h_{35}$ | ... | $h_{3E}$ |

The matrix H[j][e] in the above embodiment is an example matrix of order 3×E, for a total of three skill levels and a total of E exercises. The values $h_{ie}$ (for values of i=1, 2, 3; and e=1, 2, 3 ... E) in the matrix may be decided by the gym system in advance. Further, as stated previously, the system may impose a restriction on a particular exercise to be performed by users of only a certain skill level. Thus, the system may assign a value of zero to the corresponding number of hours for the user of a particular skill level. In other words, a value of zero for the number of hours to work for a particular exercise may imply that the particular exercise is not to be performed by the user of a particular skill level.

According to another embodiment, the gym system may assign a degree of difficulty for each exercise offered. For example, the system may assign a positive integer in the range [1-10] to signify the level of difficulty of each exercise. For instance, for a total of E=10 exercises the gym system may assign the following degree of difficulties as shown:

TABLE III

Degree of difficulty for exercises

| Exercise | Degree of Difficulty |
|---|---|
| e = 1 | 2 |
| e = 2 | 4 |
| e = 3 | 10 |
| e = 4 | 6 |
| e = 5 | 3 |
| e = 6 | 5 |
| e = 7 | 1 |
| e = 8 | 9 |
| e = 9 | 10 |
| e = 10 | 8 |

Further, the system may impose restrictions as to which exercises are performed by users based on their skill levels. For example, a user having the novice skill level (j=1) is restricted on performing an exercise having a higher degree of difficulty. According to an embodiment, the system may allocate a range of difficulties and the corresponding exercises that may be suitable for a particular skill level. However, a user having a high skill level is not restricted from performing an exercise that may be allocated to a user of a lower skill level. For the set of E=10 exercises shown in Table III, the gym system may allocate the exercises as follows:

TABLE IV

Assignment of exercises based on skill level

| Skill Level | Range of Exercise Difficulty | Exercises Assigned |
|---|---|---|
| j = 1 | 1 to 4 | e = 1, e = 2, e = 5, e = 7 |
| j = 2 | 5 to 8 | e = 4, e = 6, e = 10 |
| j = 3 | 9 to 10 | e = 3, e = 8, e = 9 |

According to an embodiment, the gym system may define a parameter: total associated degree of difficulty ($A_j$) for each of the skill levels (j=1, 2 and 3). Specifically, the predetermined value of parameter $A_j$ indicates an upper bound on the sum of degree of difficulties of all exercises performed by a user. Specifically, for each user, the sum of the degrees of difficulties of the exercises performed by the user cannot exceed the predetermined upper bound. For instance, when a user selects K exercises out of a total of E exercises the following condition must be valid.

$$TD_i = \sum_{j=1}^{K} d_j \quad (1)$$

$$TD_i \leq A_{S_i} \quad (2)$$

wherein, $TD_i$ is the total degree of difficulty of all exercises performed by user i. $A_{S_i}$ is the associated degree of difficulty for user i, with skill level $S_i$. Further, as shown in Table II, the system may require a user of a particular skill level to input minimum number of hours for an exercise to achieve the expected weight loss as shown in Table I. The values in Table I and Table II can be represented on a daily, weekly, monthly basis or the like.

When a user selects K exercises, the system may verify if the minimum number of hours required to achieve the expected weight loss is satisfied. Specifically, the required number of hours for the user selected exercises can be obtained as follows:

$$(H_{required})_i = \Sum_{k=1}^{K} H[S_i][k] \quad (3)$$

wherein, $(H_{required})_i$ is the sum of the elements of the matrix H represented in Table II, for the user of skill level $S_i$. Further, at initial user registration in the system, the user creates a profile wherein the user may input the number of hours he/she is willing to work ($H_i$). Based on this information the system verifies if the following condition is satisfied:

$$(H_{required})_i << H_i \quad (4)$$

Specifically, the number of hours input by the user must be greater than the minimum number of hours required to achieve the weight loss for the user selected exercises. The user on performing an initial registration with the system may input various parameters such as those outlined below:

TABLE V

User parameters

| Parameter | Description |
|---|---|
| $HT_i$ | Height of the user |
| $W_i$ | Initial weight of the user |
| $A_i$ | Age of the user |
| $(W_t)_i$ | Target weight to be achieved |
| $D_i$ | Number of days a week user will be in the gym |
| $H_i$ | Number of hours per day the user will exercise |
| $S_i$ | Skill Level of the user |

As shown in Table V, the parameter Skill level may be entered by the user or the user may input other information required by the system to determine the appropriate skill level of the user. Such information for example, may be, has the user exercised before, how frequently has the user exercised, does the user have any medical condition or the like.

The gym system uses the above defined parameters to compute a performance index for each user. For a set of exercises selected by the user, the system first computes an expected loss weight for each user. The expected weight loss for each user is calculated as follows:

$$(L_{expected}) = \sum_{k=1}^{K} W[S_i][k] \tag{5}$$

The system may at the end of the day, week, month or the like compute the actual weight loss achieved by the user. The actual weight loss is represented as $L_{actual}$. A difference in the expected and actual weight loss achieved by the user can be represented as $\Delta_L$. The difference is calculated as $L_{actual} - L_{expected}$. The performance index (PI) of a user can thus be represented as $$PI = (\Delta_L / W_i) * 100 \tag{6}$$

The system incorporates the performance index of a user in determining a transition in the user's skill level (described with reference to FIG. 8) and determines which exercises are suitable to be performed by the user.

Figure 6:
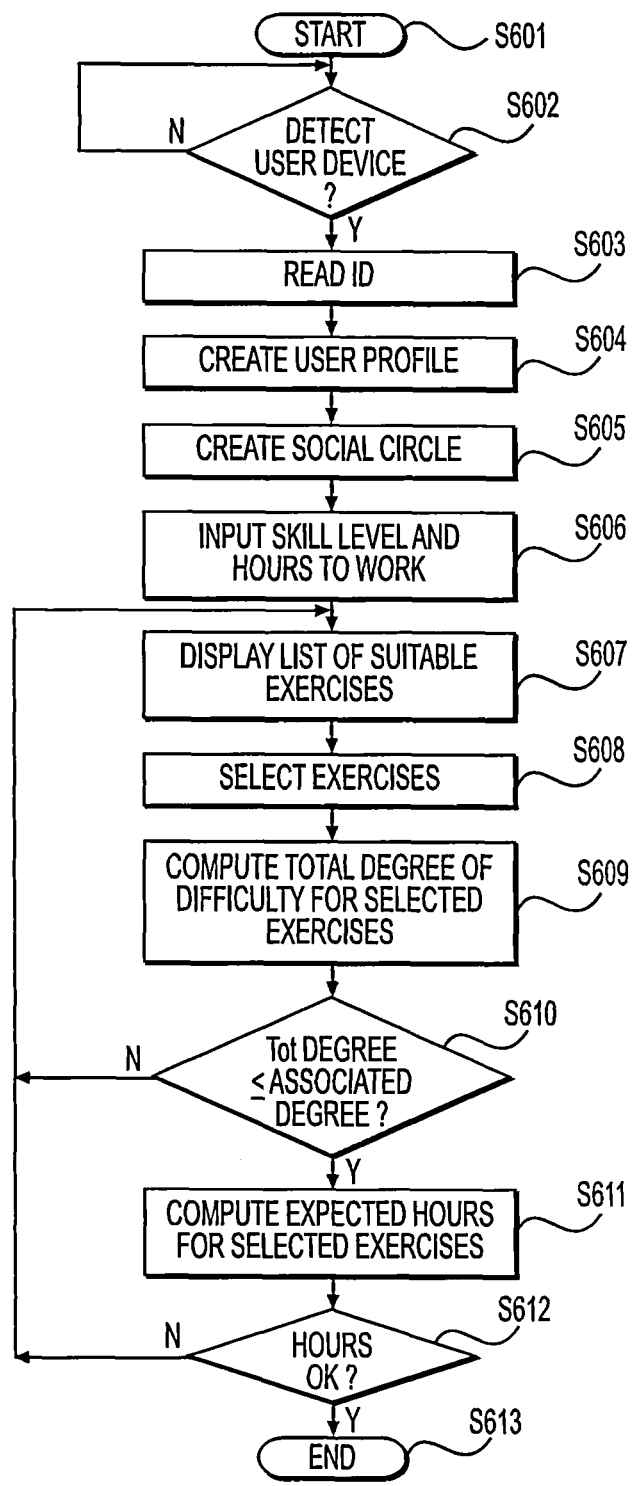
FIG. 6 is a flow chart depicting a registration process of a user according to an embodiment.

FIG. 6 is a flow chart depicting a registration process of a user according to an embodiment. The registration process may be carried out by the system controller 105 in conjunction with the interface device 200. The process starts at step S601 and proceeds to step S602.

At S602, a query is made to check if the interface 200 detects the user device 110A at the reader 350. If the response to the query is affirmative, the process moves to step S603 wherein the identification information stored in the user device is transferred to the system controller via the interface device. If the response to the query is negative, the process simply loops back and waits for the interface device to detect a user device.

At step S604, the system may display a message on the display panel 370 of the interface device prompting the user to create a profile. Upon receiving such a notification the user may input parameters listed in Table V.

The process then proceeds to step S605, wherein the user may input a social friend circle group that the user is a member of. The social friend circle can be identified by the name of the group, the user members of the group or the like. Upon inputting the social circle, the system assigns the social circle with the user profile and is further notified that the user may potentially be interested in comparing his workout activity with that of his friends and may also change his workout routine, diet or the like based on the exercises and diet of the members of the group.

In step S606, the user may input his skill level. Alternatively, the may enter required information into the system in order for the system to determine the user's skill level. The required information for example, may be, has the user exercised before, how frequently has the user exercised, does the user have any medical condition or the like. Further, the user can input the number of hours per day (or week) that the user is willing to perform the exercise.

In step S607, the system may display a list of suitable exercise to be performed by the user based on his skill level. Such exercises may be displayed based on the degree of difficulty of each exercise as outlined Tables III and IV.

In step S608, the user selects a set of exercises (based on his skill level and exercises recommended by the system) that the user is willing to perform. Based on the user's selection, in step S609 the system computed the total degree of difficulty of the exercises selected by the user as shown in equation (1).

The process then moves to step S610, wherein a query is made to check if the total degree of difficulty of the exercises selected by the user is less than the associated degree of difficulty for the user's skill level. Specifically, the system verifies if the condition as stated in equation (2) is satisfied. If the response to the query is affirmative the process moves to step S611. If the response to the query is negative, the process loops back to step S606, wherein the user is provided with the list of suitable exercise to be performed. Alternatively, the registration process may also prompt the user if he wishes to change the number of hours the user is willing work on a daily, weekly, monthly basis or the like.

In step S611, the system computes the expected number of hours to be inputted by the user on a daily, weekly, monthly basis or the like, based on the exercises selected by the user. The system performs the above calculation based on the values represented in Table II.

The process then proceeds to step S612, wherein a query is made to check if the number of hours input by the user in step S606, are greater (or equal to) than the number of hours required to perform the user selected exercises, as computed in step S611. If the response to the query is negative, the process loops back to step S607, wherein the user can view a list of all the exercises to be performed for his skill level and make another selection. Alternatively, according to another embodiment, the process may loop back to step S606, wherein the user may change the number of hours he is willing to perform the exercise in order to meet the system requirements. If the response to the query in step S612 is affirmative the moves to step S613 and the registration process terminates.

Figure 7:
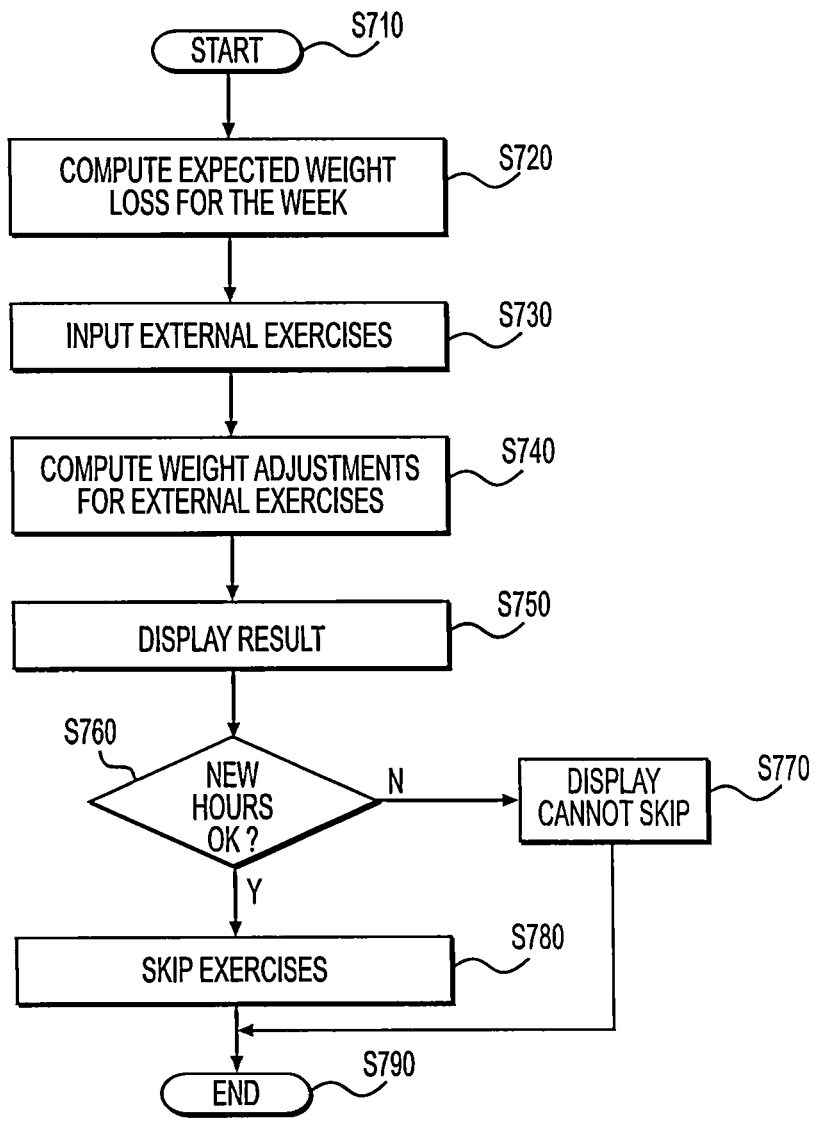
FIG. 7 is a flow chart depicting the steps performed to determine is a workout can be skipped.

FIG. 7 is a flowchart that depicts the steps performed to determine if a workout (exercise) can be skipped on a particular day.

The process begins in step S710 and proceeds to step S720, wherein the system retrieves the expected weight loss to be achieved by a user in a given week. The system may also retrieve, based on the day the user wishes to skip the workout, the number of hours of exercises performed in the week until that day.

In step S730, the user inputs external factors that correspond to the amount of activities performed outside the gym. For instance, the user may input a certain number of miles jogged, intake of food calories, and number of miles walked or the like.

The process then moves to step S740 wherein the system determines a corresponding weight loss achieved by the user for the external exercises performed outside the gym. The system may use a predetermined method of assigning a corresponding weight loss for the amount of physical activities performed outside the gym.

In step S750, the system may calculate a daily target workout amount for the next gym visit of the user 110. This daily target workout amount $W_{dt}$ may be calculated as follows:

$$W_{dt} = (W_{wt} - W_{total})/N_{rv} \tag{7}$$

where $W_{wt}$ is the weekly target workout amount, $W_{total}$ is i the total workout amount that is the sum of all the workout amounts of the exercises performed in the fitness gyms and all the physical activities performed outside the fitness gyms from the beginning of the current week to the current day, and $N_{rv}$ is the number of remaining planned gym visits in the current week excluding the current day. Based on this calculation, the system may display new number of hours that the user may need to perform the exercises if the current day is to be skipped.

In step S760, a query is made by the system to verify is the user is okay with the newly computed number of hours. If the response to the query is affirmative the process moves to step S780 wherein a message indicating skip exercises for the day is displayed on the display panel. If the response to the query is negative, a message indicating that the workout cannot be skipped is displayed on the display panel (S770). Upon completing the querying in step S760 and displaying the appropriate message the process terminates.

Figure 8:
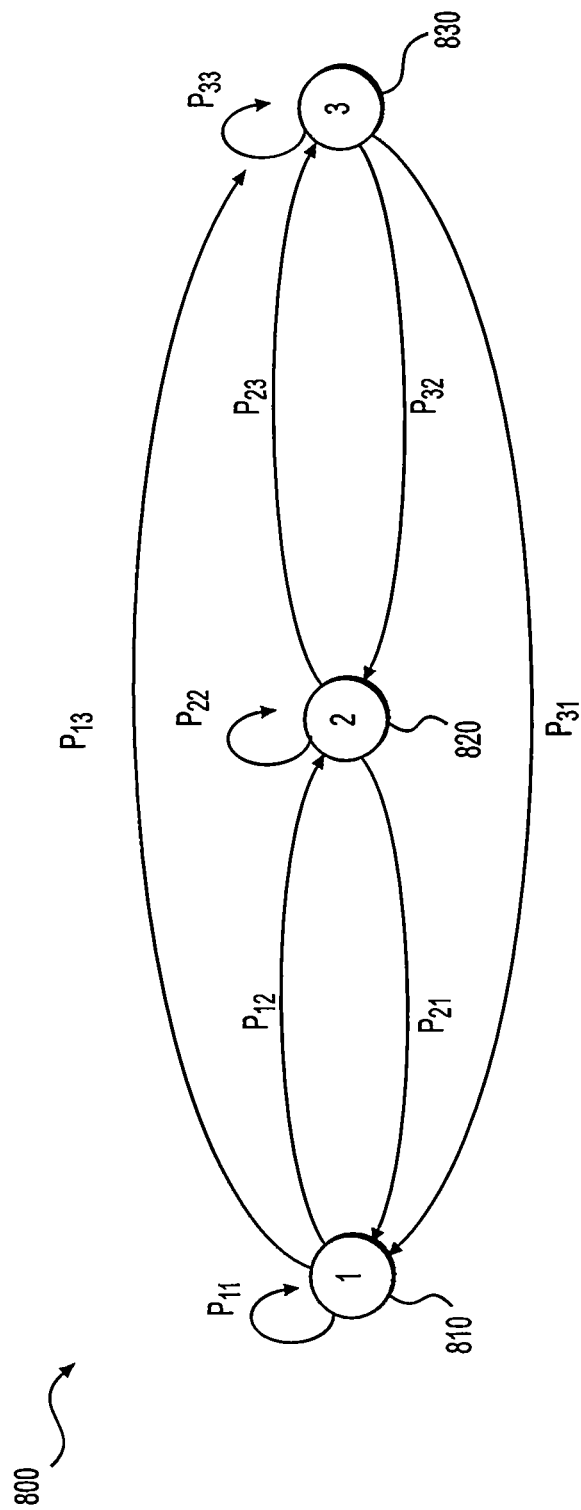
FIG. 8 is a state transition diagram depicting the transition of user's skill level.

FIG. 8 is a state transition diagram 800 depicting the transition of user's skill level according to an embodiment of the present disclosure.

In FIG. 8, three skill levels: (1) novice/beginner, (2) intermediate and (3) expert are represented as 810, 820 and 830 respectively. According to the present embodiment, to compute the transition of a user's skill level from one state to the other, the system computes an overall performance factor (OP) for the user. The overall performance factor may be based on the performance index of the user (PI), length of time the user has been in the gym (M) and the length of time the user has maintained his performance index ($\Delta T$). Specifically, the system may compute the overall performance index as a weighted sum of the above parameters as shown below:

$$OP_i = \alpha(PI_i) + \gamma(M_i) + \beta(\Delta T_i) \quad (8)$$

wherein the sum of the weighting factors $\alpha+\beta+\gamma=1$. The system may use appropriate values for the weighing factor to determine the overall performance parameter of the user. Further, for a total of three skill levels, the system may have two predetermined thresholds in order to determine if a user can make a transition from one skill level to another skill level. For instance considering thresholds T1 and T2, the transitions as outlined in Table VI may be determined. The transitions are represented by arcs as shown in FIG. 8. The notation $P_{ij}$ for the arcs in FIG. 8 represent that a user whose initial skill level is i makes a transition to skill level j based on his overall performance factor.

TABLE VI

Skill level transition thresholds

| Transitioning into skill level 1 | Transitioning into skill level 2 | Transitioning into skill level 3 |
|---|---|---|
| $P_{11} < T1$ | $T1 < P_{12} \leq T2$ | $P_{23} > T2$ |
| $P_{31} < T1$ | $T1 < P_{22} \leq T2$ | $P_{33} > T2$ |
| $P_{21} < T1$ | $T1 < P_{32} \leq T2$ | $P_{13} > T2$ |

Consider the arc $P_{12}$ emerging from state 1 and terminating in state 2. This represents that the corresponding overall performance factor of the user $P_{12}$, is greater than a first threshold T1 and less than a second threshold T2. Thus, the user is transitioned from skill level 1 to skill level 2. The transitioning of the skill level of a user permits the user in selecting different exercises as described next with reference to FIG. 9.

Figure 9:
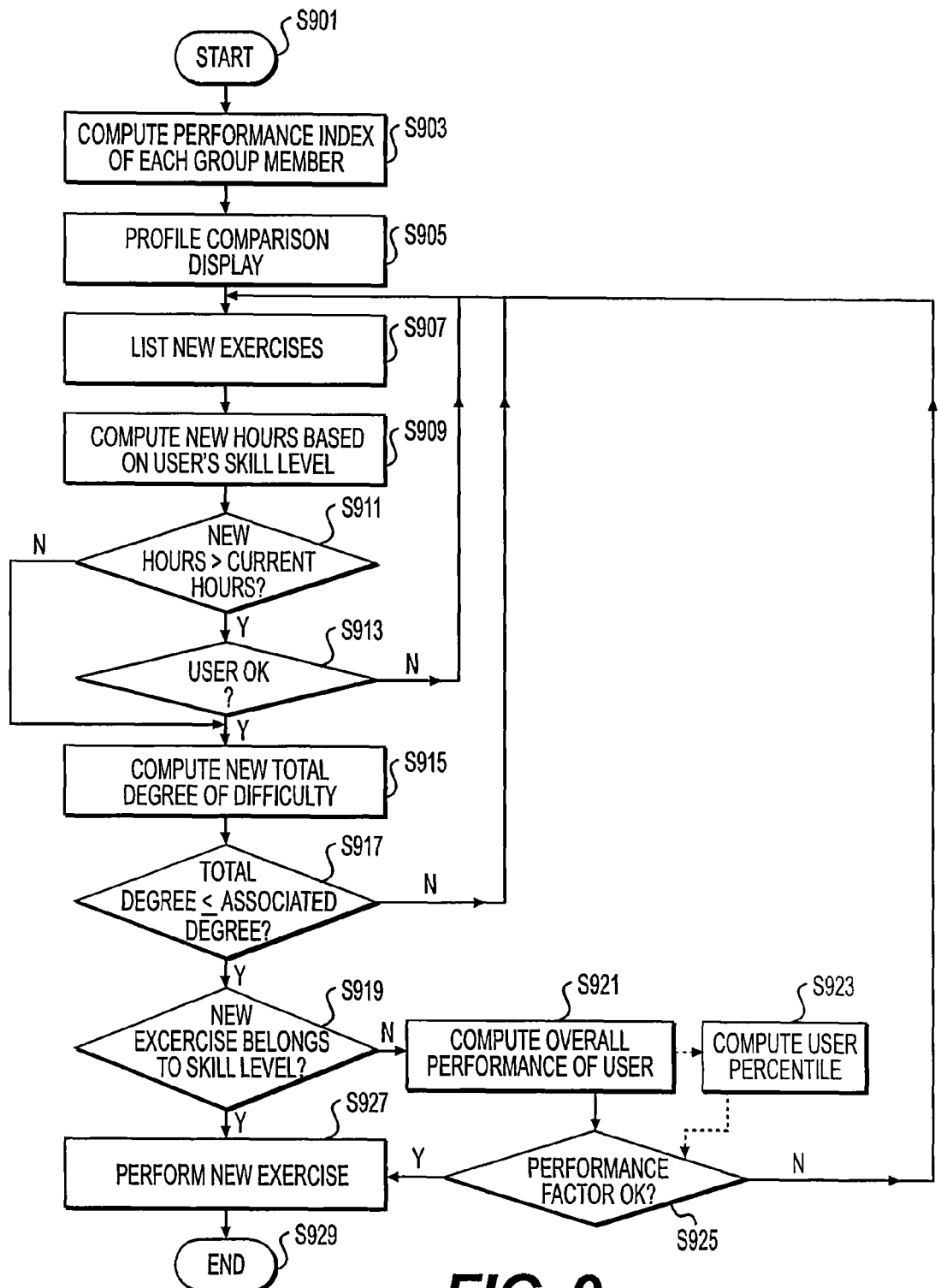
FIG. 9 is a flow chart for performing a group comparison in order to enable the user to select exercises based on the exercises performed by group members according to an embodiment.

FIG. 9 is a flow chart for performing a group comparison in order to enable the user to select exercises based on the exercises performed by group members according to an embodiment of the present disclosure.

The process begins in step S901 and proceeds to step S903 wherein the performance index of each member in the users group is computed.

Next, at step S905, the computed performance index along with other pertinent information is displayed on the display panel. Details of step S905 are described later with reference to FIG. 13A and FIG. 13B.

In step S907, the user selects a particular user from the group (friend circle) and a list of exercises that the user can potentially perform are displayed on the display panel.

In step, S909 hours required to be exercised by the user for the potential new exercises, and based on the user's skill level, are computed. The process the moves to step S911, wherein a query is made to check if the newly computed hours are greater than the number of hours the user is currently working in the gym. If the response to the query is negative, the process moves to step S915. If the response to the query is affirmative, the process moves to step S913.

In step S913, a query is made to verify is the user agrees to have an increased number of hours for the workout exercises. If the response to the query is negative, the process moves to step S907 wherein the user may select another friend from the group in order to determine new exercises to be performed. If the response to the query is affirmative, the process moves to step S915.

In step S915, the total degree of difficulty of the potential new exercises is determined and then the process moves to step S917.

In step S917, a query is made to determine if the total degree of difficulty of the new exercise is greater than the associated degree of difficulty of the user's skill level. If the response to the query is negative the process moves to step S907. If the response to the query is affirmative the process moves to step S919. According to another embodiment, step S917 may be omitted completely and the process may move from step S915 to S919.

In step S919, a query is made to determine if the new exercise selected by the user is an exercise that is assigned to the skill level of the user. If the response to the query is affirmative, the process moves to step S927 wherein a message is displayed on the display panel indicating that the user can perform the exercise. If the response to the query is negative, the process moves to step S921.

In step S921, the overall performance factor of the user is computed as shown in equation (8). The process then moves to step S925, wherein a query is made to check if the overall performance factor of the user is sufficient enough in order to enable the user to make a transition to the skill level of the new exercise. Alternatively, according to another embodiment, if the user does not make a transition to the new skill level, the system may compute if the performance index (or overall performance factor) of the user has been greater than a predetermined threshold for a certain period of time. For instance, if the user's performance index has been above 90% for the past 2 months, the user has the provision to perform an exercise of a higher skill level.

Optionally, the process outlined in FIG. 9 may perform the task in step S923, in order to determine if the user can perform an exercise of a higher skill level. According to one embodiment, the system may compute a percentile of the user based on all users that belong to the user's skill level. If the user is within a certain percentile range within the users in his group, the system may allow the user to perform an exercise of a higher degree of difficulty. Alternatively, the system may also perform the above calculations based on the height and/or weight of the user and compare it with other users having a similar height and/or weight as that of the user.

Once the process in FIG. 9 determines if the new exercise can be performed by the user, the process moves to step S927 and terminates thereafter. If the performance calculations (performed in S921, S923) are not satisfactory, the process loops back from step S925 to step S907, wherein the user is presented with a list of new potential exercises that can be performed by the user.

Figure 10:
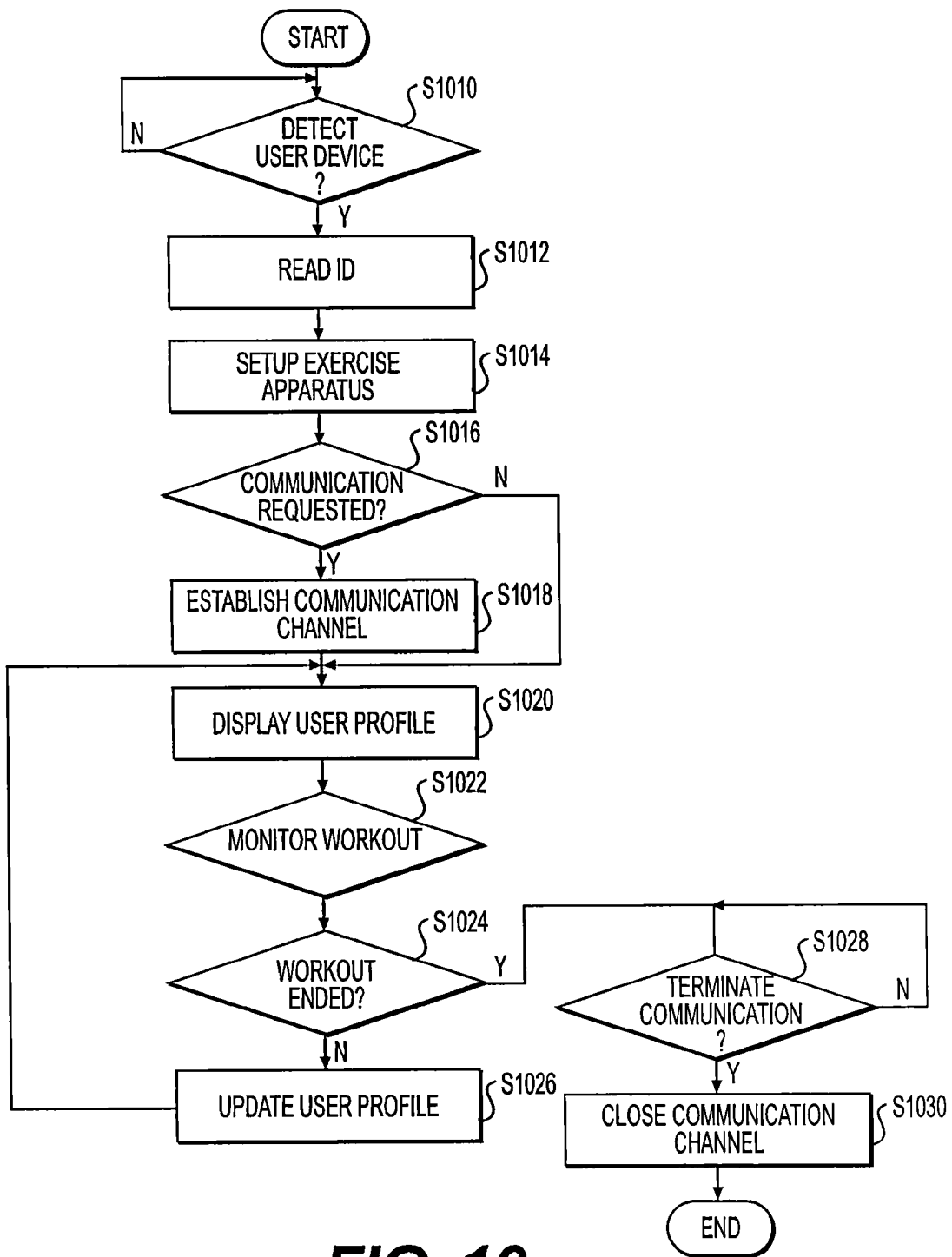
FIG. 10 is a flow chart for performing a monitoring process at an interface device in a gym exercise support system.

FIG. 10 is a flow chart for performing the monitoring process at the interface device 200 in the gym exercise support system according to an embodiment. The monitoring process is performed by the system controller 105 in conjunction with the interface device 200. The interface device 200 is coupled to one of the exercise apparatuses 104.

When the interface device 200 detects the user device 110A at the reader 310 (Yes at step S1010), the identification information stored in the user device is read out (S1012), and the system controller 105 accesses the user database 115 and obtains the user profile information corresponding to the readout identification information.

Next, the system controller 105 accesses the exercise database 117 and reads the apparatus setup parameters that correspond to the exercise apparatus 104 coupled to the interface device 200. The apparatus setup parameters are then transmitted to the interface device 200 to which the user logs in, and this interface device 200 uses the received apparatus setup parameters to set up the exercise apparatus 104 coupled thereto (S1014).

The apparatus setup parameters correspond to information required to configure the exercise apparatus 104 so as to allow the user 110 to perform a particular exercise with the exercise apparatus 104. The parameters may include, for example, but are not limited to, an exercise program to be used, a resistance or intensity during exercise, duration or number of repetitions, the inclination of the apparatus or the like. These parameters may be set for example, based on the skill level of the user.

The exercise apparatus 104 may be configured in different ways with different sets of the apparatus setup parameters, so that the user 110 may be able to perform different exercises with single exercise apparatus 104. For example, a treadmill may be set up to have a constant and slower speed for lower skill level users, whereas the same treadmill may be set up with preprogrammed variable speeds suitable for higher skill level users.

The system controller 105 determines whether the user 110 has requested a set up of a communication channel with another user of the gym exercise support system (S1016). For example, the system controller 105 may prompt the user 110 to enter information that identifies a user that he/she wishes to communicate with during the workout, using the touch-sensitive display unit 370. The system controller 105 may determine an indication of the request being input when information pertaining to a designated user is entered on the touch-sensitive display unit 370.

When the system controller 105 determines that a request has been input (Yes at step S1016), the system controller 105 accesses the user database 115 to identify the designated user with whom the current user 110 wishes to communicate. The system controller 105 further identifies the interface device 200 to which the designated user has logged in and establishes a communication channel between the interface devices 200 of the user 110 and the designated user, so as to allow the user 30 to communicate with the designated user (S1018). When the system controller 105 cannot identify the interface device 200 to which the designated user logs in, i.e., when the designated user has not been logged in the gym exercise support system, the system controller 105 informs the user 30 accordingly through the interface device 200.

The designated user may be one of users of the gym exercise support system or an in-house trainer who is using one of the interface devices 200 and may provide advices to the user 110 through the interface device 200. The designated user may not need to be in the same fitness gym as the user 110 as long as the designated user is using the interface device 200 of the gym exercise support system according to the present embodiment, which is coupled to other interface devices 200 through LAN 109 and/or the communication network 107.

When the system controller 105 determines that there is no request to establish a communication channel (No at step S1016), the process proceeds to step S1020.

Next, all or part of the user profile information including the daily workout regimen is displayed on the touch-sensitive display unit 370 to inform the user 110 of the selected exercises to be performed on a given gym visit (S1020). It is preferable that the daily workout regimen displayed includes at least a list of the selected exercises to be performed, the target durations or the target numbers of repetitions of the respective selected exercises, and actual performances of the respective selected exercises or the like.

After displaying all or part of the user profile information on the touch-sensitive display unit 370 at step S1020, the system controller 105 starts monitoring the workout of the user 110 (S1022), and determines whether the workout is continuing or ended after the elapse of a certain period of time (S1024).

According to one embodiment, the monitoring of the user workout may be carried out by measuring one or more signals that change in response to movements of user's body during the workout. For example, in the case of a treadmill, the signals may include a signal that indicates the running speed of treadmill belt and a signal that indicates the time duration in which the treadmill belt is running since the start of running. These signals may be outputted from the exercise apparatus 105 or from sensors installed in the interface device 200 to directly or indirectly measure the movements of user body during the workout.

The determination of whether the workout is still continuing or if the workout has terminates may be carried out, for example, by detecting absence of the movement in the exercise apparatus 104 over a predetermined period of time, or by prompting the user to enter an instruction when the workout is ended through the interface device 200.

When the system controller 105 determines that the workout is continuing (No at step S1024), the system controller 105 updates corresponding data of the user profile information with the newly acquired monitoring result (S1026), and the process returns to step S1020 to display the updated user profile information. For example, while using a treadmill, the performed duration of exercise is updated with the current value, and the updated performed duration is displayed in the column 1114 of the daily workout regimen 1110 of FIG. 11 (to be described). Steps S1020 to S1026 are repeated until the workout has terminated.

When the system controller 105 determines that the workout is ended (Yes at step S1024), the system controller 105 further determines whether or not the communication channel is to be terminated (S1028). When the communication channel is established at step S1018, this determination may be carried out, for example, by way of displaying a software button (icon) on the touch-sensitive display unit 370, for termination of the communication and detecting a touch operation of the icon. The established communication channel is maintained until the user instructs the termination of the communication channel (No at step S1028).

When the system controller 105 determines that the communication channel is to be terminated (Yes at step S1028), the system controller 105 controls the communication modules 230 of the interface devices 200, to terminate the communication channel (S1030) and the monitoring process terminates thereafter.

Figure 11:
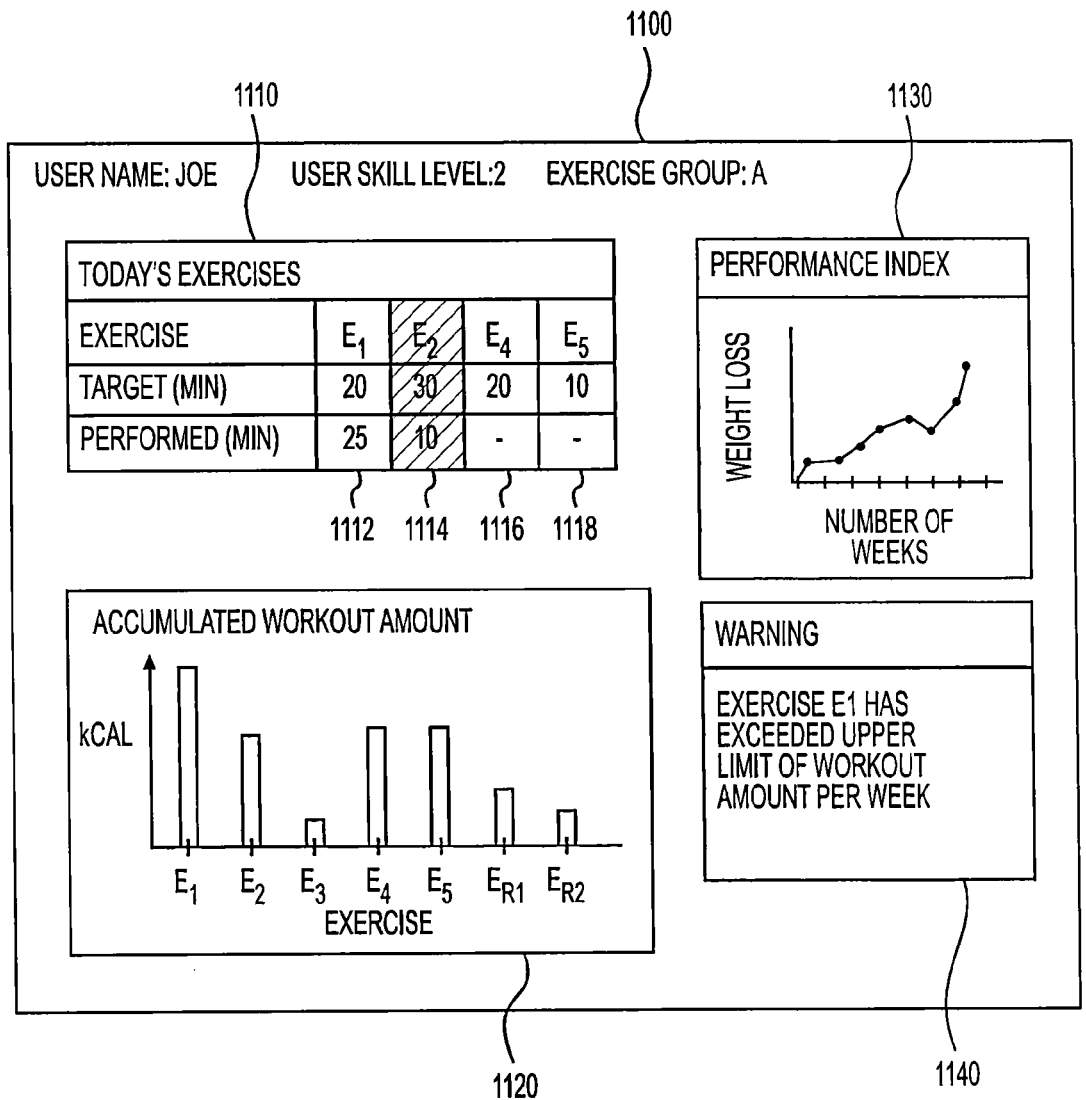
FIG. 11 is a screen image depicting user profile information displayed on an interface device according to an embodiment.

FIG. 11 is an example of a screen image 1100 of the user profile information displayed on the touch-sensitive display unit 370 of the interface device 200 according to an exemplary embodiment. In this example, the screen image 1100 of the user profile information may include, for example, the daily workout regimen 1110, an accumulated workout amount chart 1120, a performance index chart 1130, and a warning comment 1140.

The daily workout regimen 1110 is a table of the target duration and the performed duration in minutes for each of selected exercises e1, e2, e4, and e5. In this example, a column 1112 indicates that the target duration of the selected exercise e1 is 20 minutes and the workout duration actually performed is 25 minutes. A column 1114 is highlighted to indicate that the workout of the selected exercise e2 is currently being monitored and the duration thereof is being measured. Alternatively, the column 1114 may be displayed in different color or texture or size for easier recognition. Columns 116 and 118 indicate that the target durations of the selected exercises e4 and e5 are 20 minutes and 10 minutes but have not been performed.

The accumulated workout amount chart 1120 is a chart of accumulated workout amounts of all the exercises performed in the current week. In this chart 1120, the workout amount is represented by calories burned by the workout of each exercise. Furthermore, in the chart 1120, exercises eh1 and eh2 are the physical activities performed outside the fitness gyms, such as running, walking, stair climbing, etc. The chart 1120 helps the user to see which exercises the user has been performing the most in term of the calories. The chart 1120 also allows the user to see the balance of workout between the exercises in the fitness gyms and the physical activities performed outside the fitness gyms.

The performance index chart 1130 is a chart illustrating the change in the performance index score over time, and helps the user to measure the progress of the workout. In this example, the selected performance index is the weight loss since the start of gym exercising. Alternatively, any other performance index such as the weekly weight loss, the weekly accumulated workout amount, the ratio of the weight loss to the total workout amount, etc., may be selected and displayed.

The warning message 1140 is a message to warn the user 110 when any of the exercises the user 30 has been performing in the current week exceeds the preset upper limit of workout amount. The upper limit of workout amount may be determined in advance for each skill level and each exercise. Presenting such a warning message may prevent the user 30 from overworking a certain exercise. The upper limit of workout amount may be varied depending of the type of exercise, for some types of exercises are more difficult to perform or prone to accidents. Alternatively, the screen image 1100 may include additional pieces of information that are already included in the user profile information or data newly derived from the user profile information.

Figure 12:
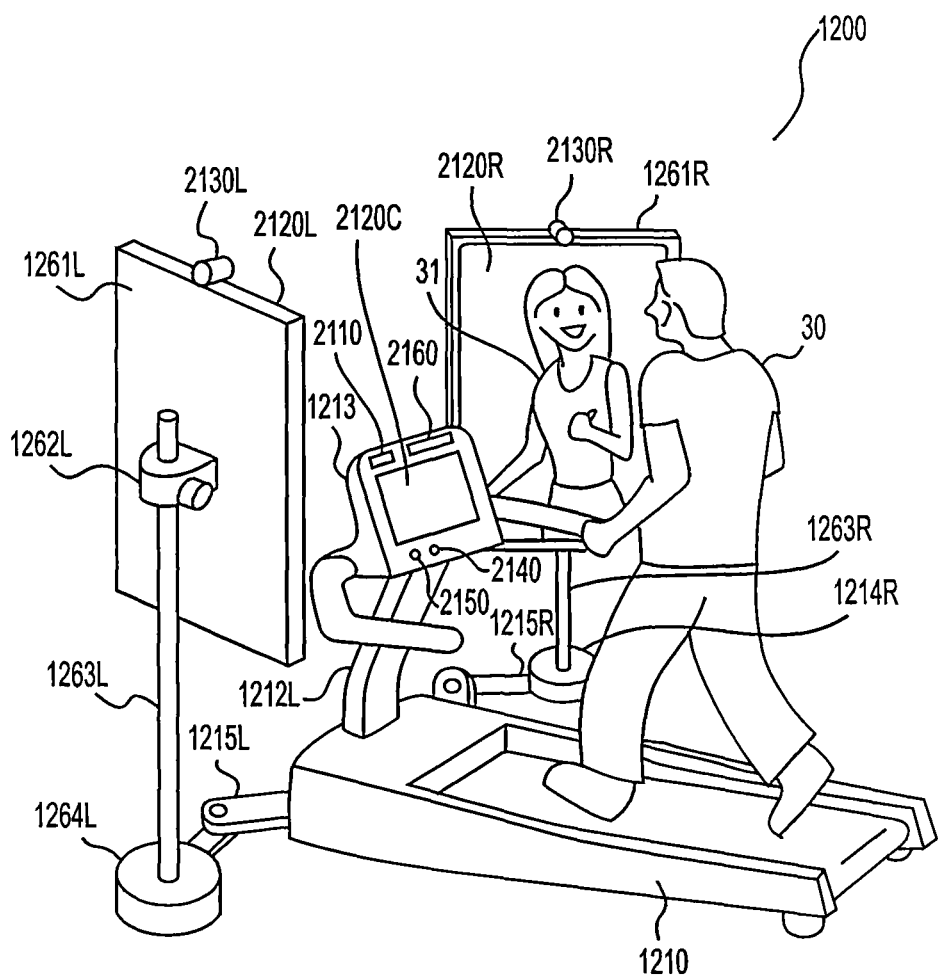
FIG. 12 is a perspective view of an exercise apparatus according to an embodiment of the disclosure.

FIG. 12 is a perspective view of the exercise apparatus 1200 according to one embodiment. The exercise apparatus 1200 is provided with substantially all the functionalities performed by the foregoing interface device 200 and coupled to the system controller 105 through the LAN 109 and/or the communication network 107.

In a particular example illustrated in FIG. 12, the exercise apparatus 1200 is a treadmill. FIG. 12 depicts a scenario where a user 30 is running on a treadmill belt and having conversations with another user 31 who is using another exercise apparatus of the present embodiment. The exercise apparatus 1200 and another exercise apparatus may be placed in the same fitness gym or different fitness gyms. The user 31 may be performing the same or different exercise from that of the user 30.

As illustrated in FIG. 12, the exercise apparatus 1200 includes a main body 1210, a control terminal 1213, display units 1261R, 1261L, and cameras 2130R, 2130L. The control terminal 1213 is supported on a front side of the main body 1210 by a fixed arm 1212. The display units 1261R and 1261L are respectively supported by movable arms 1215R and 1215L that are attached on lower sides of the main body 1210. The cameras 2130R and 2130L are respectively arranged on upper sides of the display units 1261R and 1261L.

The control terminal 1213 includes a reader 2110 for reading the identification information stored in the user device 110, a touch-sensitive display unit 2120C, a microphone 2140, a speaker 2150, and a printer 2160. The touch-sensitive display unit 2120C is used to display information such as the daily workout regimen or any other data included in the user profile information and receive input from the user with its touch-sensitive screen.

Alternatively, the reader 2110 may be a device that carries out biometric authentication such as finger print identification. In this case, the user does not need to carry the user device 110 to log in the gym exercise support system.

The display units 1261R and 1261L respectively include display screens 2120R and 2120L, link portions 1262R and 1262L, pole portions 1263R and 1263L, base portions 1264R and 1264L. The display screens 2120R and 2120L are linked to the pole portions 1263R and 1263L through the link portions 1262R and 1262L, respectively. Heights and angles of the display screens 2120R and 2120L may be adjusted by adjusting the link portions 1262R and 1262L, respectively.

The display screens 2120R and 2120L are supported by the pole portions 1263R and 1263L, and the pole portions 1263R and 1263L are securely supported by the base portions 1264R and 1264L. The base portions 1264R and 1264L are connected to the main body 1210 through the movable arms 1215R and 1215L so as to securely support the display units 1261R and 1261L at diagonally forward right and left positions from the main body 1210. Each of the display screens 2120R and 2120L diagonally faces toward the user 30 who are exercising with the main body 1210 of the present exercise apparatus so as to allow the user 30 to easily watch each of the display screens 2120R and 2120L even during the workout.

The cameras 2130R and 2130L are respectively fixed on the upper parts of the display screens 2120R and 2120L with holders which are not illustrated in the view. The holders hold the cameras 2130R and 2130L so that the cameras 2130R and 2130L may be rotated to different directions for adjustment. In a typical case, the cameras 2130R and 2130L face the same directions as those of the display screens 2120R and 2120L, respectively. For example, the cameras 2130R and 2130L may take still images or moving images of the user 30 during the workout from the waist up.

In a typical setting, the cameras 2130R and 2130L are fixed at higher than the line of sight of the user 30 and take images obliquely downward. In other words, these images of the user 30 taken by the cameras 2130R and 2130L may be slightly different from natural images that another user 31 would see if they were actually exercising together side by side. To alleviate such unnaturalness of the images, in another embodiment, the exercise apparatus 1200 may further include an image processing module for correcting the obliquely downward shot images to images substantially the same or similar to horizontal shot images taken at even height. Alternatively, the cameras 2130R and 2130L may be provided with an optics system for correcting the obliquely downward-shot images.

The foregoing configuration of the exercise apparatus 1200 allows the user 30 to call another user 31 by using the control terminal 1213. Another user 31 may be also exercising on another exercise apparatus similar to the present exercise apparatus 1200. Still images or moving images of the user 30 taken by the camera 2130R or 2130L may be sent to another exercise apparatus of another user 31 while still images or moving images of another user 31 may be displayed on the display screen 2120R or 2120L. Similarly, voices of the user 30 may be collected by the microphone 2140 and sent to another exercise apparatus while voices of another user 31 may be outputted from the speaker 2150. Accordingly, the user 30 may perform the exercise while having conversations with another user 31 who may also be exercising with another exercise apparatus.

There are following advantageous effects of performing an exercise while having conversations with another user. In general, the workout with an exercise apparatus may involve repetitions of simple movement and tends to be tedious. However, in the present embodiment, the user 30 may be able to have conversations with another user while exercising, thereby preventing the user 30 from boredom. For example, a long distance running may be a difficult exercise when performing the exercise alone, but may be easier with a companion.

In the present embodiment, the exercise apparatus 1200 is described as a treadmill apparatus. Alternatively, the exercise apparatus of the present embodiment may be, but not limited to, a bicycle apparatus, a stepper apparatus, and a weight machine. For example, one of the communicating users may be exercising with a bicycle type exercise apparatus according to the present embodiment whereas the other user may be exercising with a stepper type exercise apparatus according to the present embodiment. During the workout, the user stays at substantially the same position on the exercise apparatus. Thus, the foregoing communication between users of the gym exercise support system may be carried out using the fixed display screen 2120R or 2120L and the fixed camera 2130R or 2130L while both the users are exercising, as described in the present embodiment.

In the present embodiment, two display units 1261R and 1261L are employed and arranged diagonally forward right and left from the main body 1210 so that the display screens 2120R and 2120L obliquely face the user 30 who is exercising with the exercising apparatus 1200.

One of reasons to have this arrangement is as follows. When the display unit is placed next to the main body 1210 on the right side or the left side, the user 30 has to turn his head sideways during the workout to communicate with another user. This may hurt or cause an injury in the neck. On the other hand, when the display unit is arranged directly in front of the main body 1210, the user 30 will see another user running toward the user 30 in the case where another user is exercising with a treadmill type exercise apparatus. This arrangement may make the user 30 feel unnatural and uncomfortable. The positions and the directions of the display units 1261R and 1261L of the present embodiment may make the user 30 feel more natural when communicating with another user during exercise.

Another reason to have this arrangement is that the display screen 2120R on which the user 31 is being displayed and the display unit of the other exercise apparatus on which the user 30 is being displayed face opposite directions. That is, when the user 30 and the user 31 are communicating to each other as in the scene illustrated in FIG. 12, the user 30 faces the display screen 2120R arranged diagonally forward right from the main body 1210 to see the user 31 and the camera 2130R takes images of the user 30 whereas the user 31 faces, on her exercise apparatus, a display screen 2120L placed diagonally forward left from a main body 1210 to see the user 30 and a camera 2130L takes images of the user 31.

Alternatively, instead of having two display units 1261R and 1261L, only one of two display units 1261R and 1261L may be used. In this case it is preferable that the exercise apparatus 1200 further includes a drive mechanism for driving the movable arm connecting the display unit and the main body 1210, and that the movable arm is driven so as to move the display unit between the diagonally forward right and left positions as in the foregoing example.

In the present embodiment, the system controller 105 determines which display unit should be used for communication in each exercise apparatus by prompting the user to enter a selection of the display unit to be used or by detecting the direction the user 30 is facing using one or both the cameras 2130R and 2130L.

Furthermore, in the example of FIG. 12, the display unit 1261L that is not used for the communication may be advantageously used to display still images or moving images, for example, of nature scenery flowing laterally across the screen so as present a virtual feeling to the user of performing the exercise outdoors. Alternatively, the display unit 1261L may be used to display still another user so as to allow the user 30 to have communications with two other users displayed on the display units 1261R and 1261L.

Alternatively, according to another embodiment, while using the aforementioned setting of FIG. 12, the control unit 1213 of a given exercise apparatus that is in communication with another exercise apparatus also provisions for the user to track the performance of the other user. Specifically, the performance index of the user 31 can be displayed on the display panel of the user's 30 exercise apparatus. Furthermore, when both user's are performing similar exercises, the user 30 can extract the apparatus parameters for user 31 from the controller and incorporate those parameters in his/her apparatus if required. This provides the user an option to change his/her workout routing in a real-time and provides the user with a more interactive workout experience.

Figure 13A:
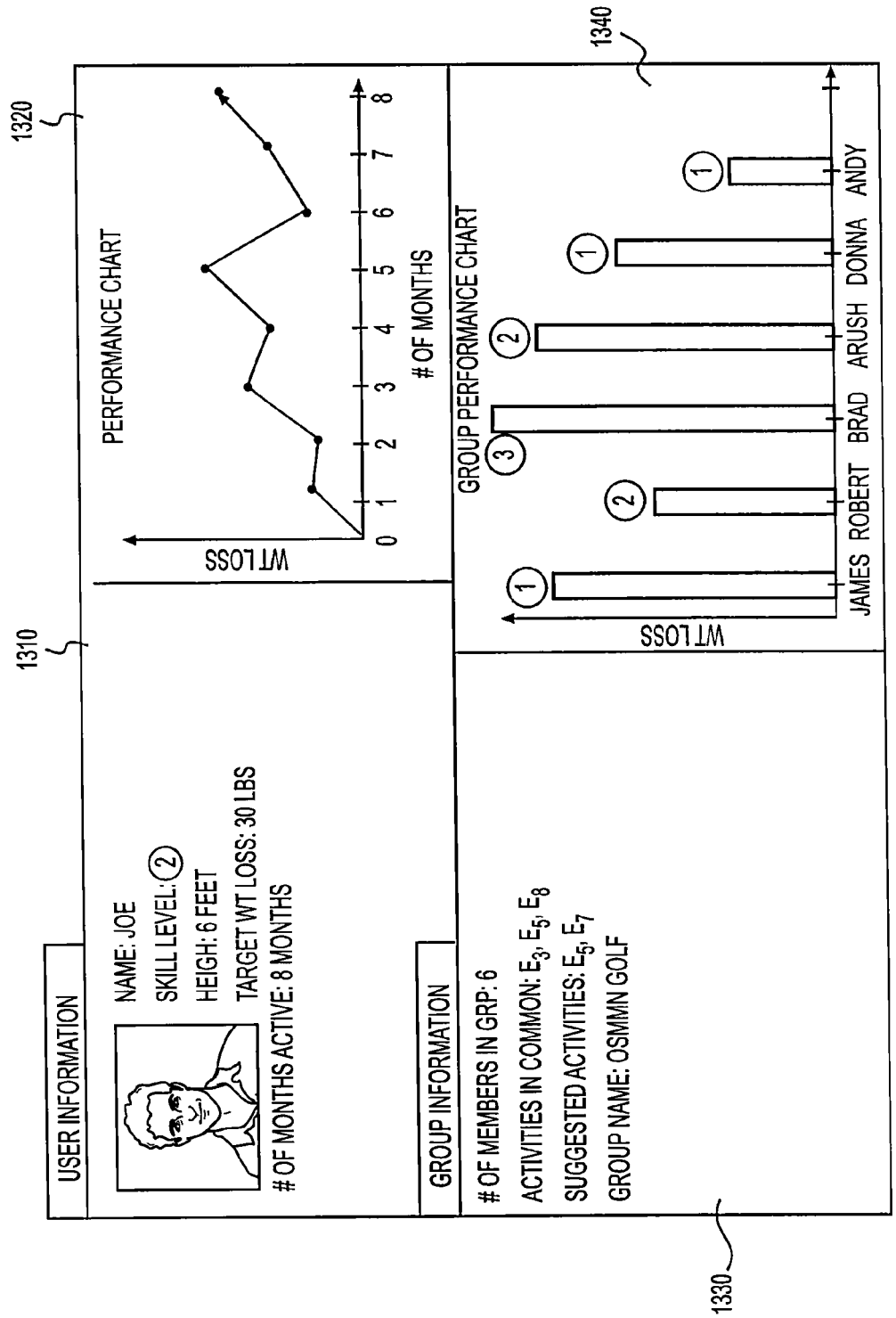
FIG. 13A is a screen image depicting user profile information and group information displayed on an interface device according to an embodiment.

FIG. 13A is a screen image depicting user profile information and group information displayed on an interface device according to an embodiment. This information can be displayed for example, when the user initiates a request to display group information on the display panel.

The screen image depicted in FIG. 13A includes the user profile information shown in 1310 and 1320, as well as group information depicted in 1330 and 1340.

In 1310, a picture of the user along with the name of the user, skill level of the user, height, and target weight loss of the user may be depicted. The information in 1320 depicts a chart showing the performance of the user in terms of weight loss over a certain period of time. This enables the user to track his performance and make necessary adjustments to his/her workout schedule.

The group information displayed in 1330 includes the group name, the number of other members in the group, the exercises that are commonly performed by members of the group, suggested exercises to be performed based on the performance index of each user in the group and the like.

In 1340, a pictorial representation, in the form of a bar chart is displayed. Specifically, the name of the group member along with his/her weight loss achieved thus far is represented as bar. Also included at the top of the bar is the member's skill level. Presenting information in this manner allows the user to select a particular member of interest and monitor his/her workout regimen and adjust the user's workout based on the performance index, weight loss or the like of the selected member.

Figure 13B:
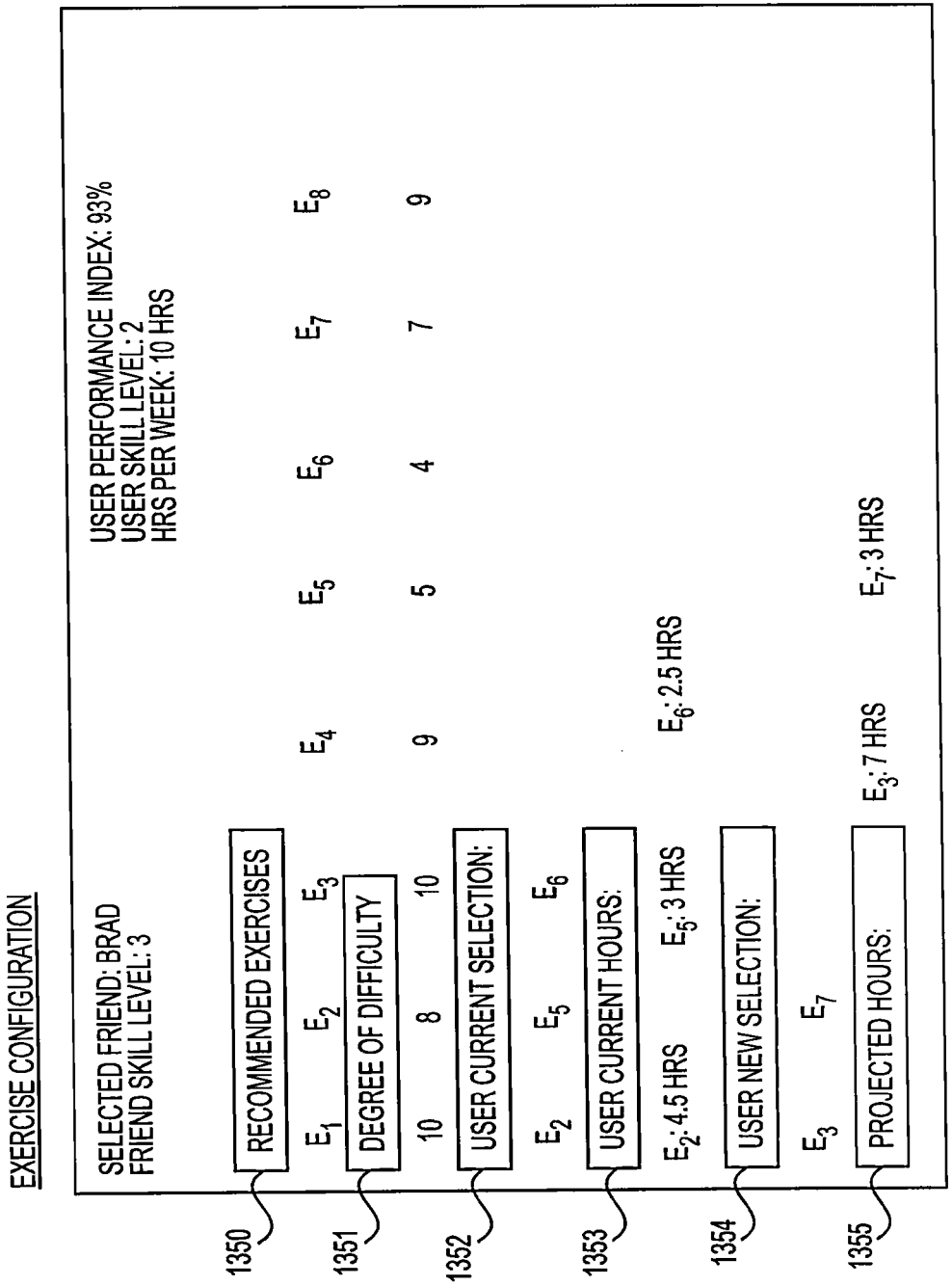
FIG. 13B depicts a screen image showing an exercise configuration for a user.

FIG. 13B depicts a screen image showing an exercise configuration performed by a user. In the example depicted in FIG. 13B, the current user (Joe) has selected friend (Brad) for determining his workout regimen.

The name of the friend selected along with the friend's skill level is displayed in the top left corner of the screen. In the top right corner of the screen is displayed user information such as the performance index of the user, the skill level of the user and the number of hours per week that the user is currently devoting for performing gym exercises.

Displayed with the above information is a series of exercises 1350 that are recommended to the user. This recommendation can be based on the exercises performed by the friend as well as the skill level of the user.

In 1351, the degree of difficulty of the recommended exercises is displayed. In 1352, the exercises currently performed by the user are displayed along with the current hours devoted for each exercise displayed below it in 1353.

As shown in FIG. 13B, the user currently performs exercises $E_2$, $E_5$ and $E_6$ which have a level of difficulty of 8, 5 and 4 respectively. Thus the user's total degree of difficulty is 17 and the number of hours devoted for these exercises is 10 hours.

Based on the choices provided in 1350, the user may select, for instance, exercise $E_3$ and $E_7$, which have a projected hours to be devoted of 7 hours and 3 hours respectively as shown in 1355.

In the example depicted in FIG. 13B, the user has a skill level of 2, whereas the selected friend has a skill level of 3. Further, the user selects $E_3$ as one of his new exercises. The user may be allowed to select an exercise of a higher degree of difficulty, as either his overall performance factor (and/or performance index) may be above a certain threshold, or the user's performance percentile within his skill level or the like may be above a predetermined threshold. Thus, by implementing the foregoing technique of comparing the user's performance to that of other group members allows the user to change his workout regime based on which exercises are being performed by the other members as well the performance index of other user's.

Figure 14:
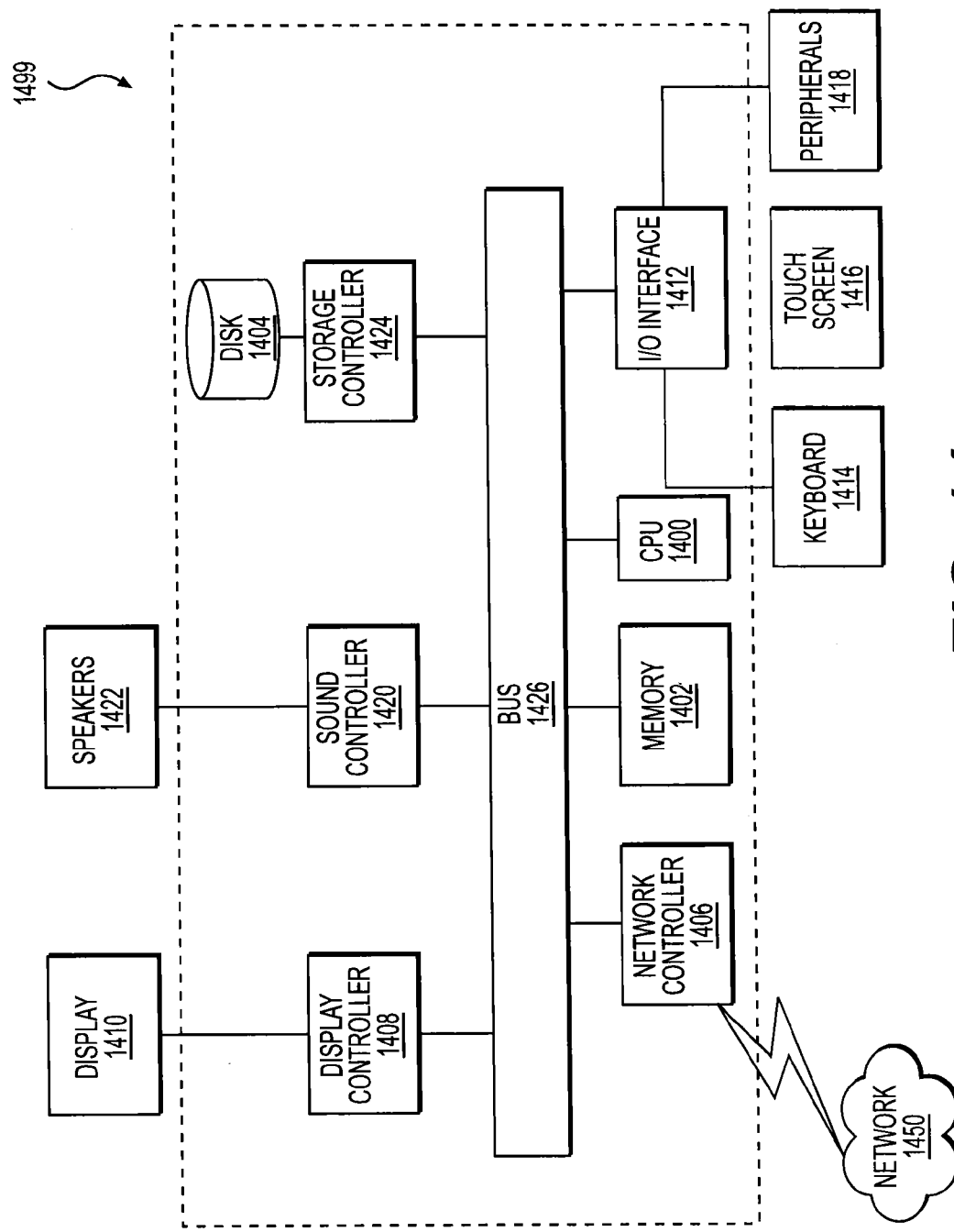
FIG. 14 illustrates a block diagram of a computing device according to one embodiment.

The embodiments discussed herein may also be performed by a general purpose computer or a mobile device that may establish a connection with a centralized system processor. Specifically, each of the program or algorithm based elements of the above noted description can be implemented by hardware such as the hardware found in the description of FIG. 14. In FIG. 14, the computer 1499 includes a CPU 1400 which performs the processes described above. The process data and instructions may be stored in memory 1402. These processes and instructions may also be stored on a storage medium disk 1404 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the system communicates, such as a server or computer.

Further, the claimed advancements may be provided as a utility application, background daemon, or component of an operating system, or combination thereof, executing in conjunction with CPU 1400 and an operating system such as Microsoft Windows 7, UNIX, Solaris, LINUX, Apple MAC-OS and other systems known to those skilled in the art.

CPU 1400 may be a Xenon or Core processor from Intel of America or an Opteron processor from AMD of America, or may be other processor types that would be recognized by one of ordinary skill in the art. Alternatively, the CPU 1400 may be implemented on an FPGA, ASIC, PLD or using discrete logic circuits, as one of ordinary skill in the art would recognize. Further, CPU 1400 may be implemented as multiple processors cooperatively working in parallel to perform the instructions of the inventive processes described above.

The computer 1299 in FIG. 12 also includes a network controller 1406, such as an Intel Ethernet PRO network interface card from Intel Corporation of America, for interfacing with network 1450. As can be appreciated, the network 1450 can be a public network, such as the Internet, or a private network such as an LAN or WAN network, or any combination thereof and can also include PSTN or ISDN sub-networks. The network 1450 can also be wired, such as an Ethernet network, or can be wireless such as a cellular network including EDGE, 3G and 4G wireless cellular systems. The wireless network can also be WiFi, Bluetooth, or any other wireless form of communication that is known.

The computer 1499 further includes a display controller 1408, such as a NVIDIA GeForce GTX or Quadro graphics adaptor from NVIDIA Corporation of America for interfacing with display 1410, such as a Hewlett Packard HPL2445w LCD monitor. A general purpose I/O interface 1412 interfaces with a keyboard and/or mouse 1414 as well as a touch screen panel 1416 on or separate from display 1410. General purpose I/O interface also connects to a variety of peripherals 1418 including printers and scanners, such as an OfficeJet or DeskJet from Hewlett Packard.

A sound controller 1420 may also be provided in the computer 1499, such as Sound Blaster X-Fi Titanium from Creative, to interface with speakers/microphone 1422 thereby providing sounds and/or music. The speakers/microphone 1422 can also be used to accept dictated words as commands for controlling the robot-guided medical procedure system or for providing location and/or property information with respect to the target property.

The general purpose storage controller 1424 connects the storage medium disk 1404 with communication bus 1426, which may be an ISA, EISA, VESA, PCI, or similar, for interconnecting all of the components of the robot-guided medical procedure system. A description of the general features and functionality of the display 1410, keyboard and/or mouse 1414, as well as the display controller 1408, storage controller 1424, network controller 1406, sound controller 1420, and general purpose I/O interface 1412 is omitted herein for brevity as these features are known.

The functions and features described herein may also be executed by various distributed components of a system. For example, one or more processors may execute these system functions, wherein the processors are distributed across multiple components communicating in a network. The distributed components may include one or more client and/or server machines, in addition to various human interface and/or communication devices (e.g., display monitors, smart phones, tablets, personal digital assistants (PDAs)). The network may be a private network, such as a LAN or WAN, or may be a public network, such as the Internet. Input to the system may be received via direct user input and/or received remotely either in real-time or as a batch process. Additionally, some implementations may be performed on modules or hardware not identical to those described. Accordingly, other implementations are within the scope that may be claimed. Furthermore, the described embodiments herein may be modified wherein the user is provided with an option to rate the difficulty of the exercise.

It should be noted that, as used in the specification and the appended claims, the singular forms "a," "an," and "the" include plural referents unless the context clearly dictates otherwise.

Thus, the foregoing discussion describes merely embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure including any readily discernible variants of the teachings herein, define, in part, the scope of the foregoing claim terminology such that no inventive subject matter is dedicated to the public.

The invention claimed is:

1. A controller device comprising:
   circuitry configured to
      list a plurality of exercises that are available to be performed by a user based on a skill level of the user;
      receive a selection of the plurality of exercises from the user and determine whether the selected exercises are permitted to be performed by the user;
      compute a performance index for the user based on a target weight loss and an actual weight loss achieved by the user;
      compute an overall performance of the user based on the performance index, a first parameter and a second parameter;
      determine whether the exercises performed by the user are permitted to be skipped for a predetermined time based on the performance index of the user;
      determine, based on the overall performance of the user whether there is a transition in the user's skill level;
      read a user device to identify setup parameters of an exercise apparatus;
      determine the user's exercises for future performance based on exercises performed by members of a group;
      adjust the exercise apparatus based on the read setup parameters and the determined user's exercises.

2. The controller of claim 1, wherein the circuitry is configured to determine whether the selected exercises are permitted to be performed by the user based on a total degree of difficulty of the selected exercises and an associated degree of difficulty corresponding to the skill level of the user.

3. The controller of claim 1, wherein the circuitry is further configured to assign a degree of difficulty for each exercise of the plurality of exercises.

4. The controller of claim 1, wherein the circuitry is further configured to receive monitoring information of the user while using the exercise apparatus.

5. The controller of claim 1, wherein the circuitry is further configured to determine, based on the user's skill level, set-up parameters for an exercise device.

6. The controller of claim 5, wherein the circuitry is further configured to change the set-up parameters of the user's exercise device in real time, based on the set-up parameters of another user's exercise device.

7. The controller of claim 1, wherein the circuitry computes the overall performance of the user as a weighted sum of the performance index, the first parameter and the second parameter.

8. The controller of claim 7, wherein the first parameter is a first duration that the user has been performing exercises and the second parameter is a second duration for which the user has maintained the performance index above a predetermined threshold.

9. The controller of claim 1, wherein the circuitry determines the exercises for future performance by the user based on the skill level of the user and the performance index of the members of the group.

10. The controller of claim 1, wherein the circuitry determines whether the exercises performed by the user are permitted to be skipped based on physical activity performed and a diet of the user.

11. The controller of claim 1, wherein the circuitry is further configured to monitor information indicating whether the exercise performed by the user exceeds a predetermined upper limit.

12. The controller of claim 1, wherein the skill level of the user is one of a beginner (low), an intermediate (medium) and an expert (high) level.

13. The controller of claim 12, wherein the circuitry is further configured to prohibit the user of the low skill level from performing exercises assigned to the high skill level.

14. The controller of claim 13, wherein the circuitry does not prohibit the user having the low skill level from performing exercises assigned to the high skill level based on whether the overall performance of the user is greater than a predetermined threshold.

15. The controller of claim 14, wherein the circuitry is further configured not to prohibit the user of low skill level from performing exercises assigned to the high skill level based on whether a user performance percentile is within a predetermined range.

16. The controller of claim 1, wherein the circuitry determines that the transition in the user's skill level occurs based on two predetermined thresholds.

17. The controller device of claim 1, wherein the circuitry is further configured to establish a communication channel with another user and monitor the workout of the other user.

18. A method of determining a workout routine comprising:
   listing a plurality of exercises that are available to be performed by a user based on a skill level of the user;
   receiving a selection of the plurality of exercises from the user and determining whether the selected exercises are permitted to be performed by the user;
   computing a performance index for the user based on a target weight loss and an actual weight loss achieved by the user;
   computing an overall performance of the user based on the performance index, a first parameter and a second parameter;
   determining whether the exercises performed by the user are permitted to be skipped for a predetermined time based on the performance index of the user;
   determining, based on the overall performance of the user whether there is a transition in the user's skill level;
   reading a user device to identify setup parameters of an exercise apparatus;

determining the user's exercises for future performance based on exercises performed by members of a group; and adjusting the exercise apparatus based on the read setup parameters and the determined user's exercises.

19. The method of claim 18, further comprising:

receiving monitoring information of the user using the exercise apparatus;

computing exercise set-up parameters for an exercise device; and prohibiting the user having the low skill level from performing exercises assigned to the high skill level based on whether a user performance percentile is within a predetermined range.

20. A non-transitory computer readable medium having stored thereon a program that when executed by a computer causes the computer to execute a method, the method comprising:

listing a plurality of exercises that are available to be performed by a user based on a skill level of the user;

receiving a selection of the plurality of exercises from the user and determining whether the selected exercises are permitted to be performed by the user;

computing a performance index for the user based on a target weight loss and an actual weight loss achieved by the user;

computing an overall performance of the user based on the performance index, a first parameter and a second parameter;

determining whether the exercises performed by the user are permitted to be skipped for a predetermined time based on the performance index of the user;

determining, based on the overall performance of the user whether there is a transition in the user's skill level;

reading a user device to identify setup parameters of an exercise apparatus;

determining the user's exercises for future performance based on exercises performed by members of a group; and adjusting the exercise apparatus based on the read setup parameters and the determined user's exercises.

\* \* \* \* \*